(12) United States Patent
Hakamata

(10) Patent No.: US 6,529,768 B1
(45) Date of Patent: Mar. 4, 2003

(54) METHOD AND APPARATUS FOR ACQUIRING FLUORESCENCE IMAGES

(75) Inventor: Kazuo Hakamata, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 191 days.

(21) Appl. No.: 09/715,056

(22) Filed: Nov. 20, 2000

(30) Foreign Application Priority Data

Nov. 18, 1999 (JP) ............................................ 11-328413
Mar. 13, 2000 (JP) ........................................ 2000-069101

(51) Int. Cl.⁷ .............................. A61B 6/00; A61B 5/00
(52) U.S. Cl. ...................................... 600/476; 600/310
(58) Field of Search ................................ 600/476, 477, 600/478, 101, 108, 109, 160, 178, 310, 312; 250/337, 338.1, 339.02, 340, 341.1, 370.08, 370.09; 348/65, 67, 68, 69, 70, 77

(56) References Cited

U.S. PATENT DOCUMENTS

| | | | | |
|---|---|---|---|---|
| 4,825,291 A | * | 4/1989 | Mimura et al. ........... | 250/206.1 |
| 4,845,553 A | * | 7/1989 | Konomura et al. ............ | 348/71 |
| 5,070,414 A | | 12/1991 | Tsutsumi .................... | 358/466 |
| 5,131,755 A | | 7/1992 | Chadwick et al. .......... | 356/394 |
| 5,608,453 A | | 3/1997 | Gerber et al. ................ | 348/87 |
| 5,647,368 A | * | 7/1997 | Zeng et al. .................. | 600/476 |
| 5,686,958 A | * | 11/1997 | Shibasaki et al. ............. | 348/45 |
| 5,699,798 A | | 12/1997 | Hochman et al. ........ | 128/653.1 |
| 5,827,190 A | | 10/1998 | Palcic et al. ................ | 600/476 |
| 5,833,617 A | | 11/1998 | Hayashi ...................... | 600/476 |
| 5,990,952 A | * | 11/1999 | Hamasaki .................... | 348/311 |
| 6,097,875 A | * | 8/2000 | Matsui ......................... | 360/47 |
| 6,280,378 B1 | * | 8/2001 | Kazuhiro et al. ............. | 348/65 |
| 6,292,169 B1 | * | 9/2001 | Numazaki et al. .......... | 250/200 |
| 6,331,818 B1 | * | 12/2001 | Hiraga .................... | 340/573.1 |

FOREIGN PATENT DOCUMENTS

DE 195 34 114 A1 3/1996 ............ A61B/1/04

* cited by examiner

*Primary Examiner*—Sang Paik
(74) *Attorney, Agent, or Firm*—Sughrue Mion, PLLC

(57) ABSTRACT

Intrinsic fluorescence, which has been produced from living body tissues when excitation light is irradiated to the living body tissues, is detected with an image sensor and is read out as an image. The image is acquired by setting the image sensor such that a reading frequency, an area of one pixel, a total number of pixels, a number of pixels subjected to pixel binning, a number of reading ports, an exposure time, a quantum efficiency, an electron multiplication factor, and a sensor temperature of the image sensor satisfy the following condition formula:

$$RN + DN < 0.22 \times P \times H \times G$$

in which RN represents the number of electric charges occurring due to reading noise, DN represents the number of electric charges occurring due to dark noise, P represents the irradiation output of the excitation light (in mW), H represents the quantum efficiency of the image sensor, and G represents the electron multiplication factor of the image sensor.

23 Claims, 13 Drawing Sheets

F I G. 4
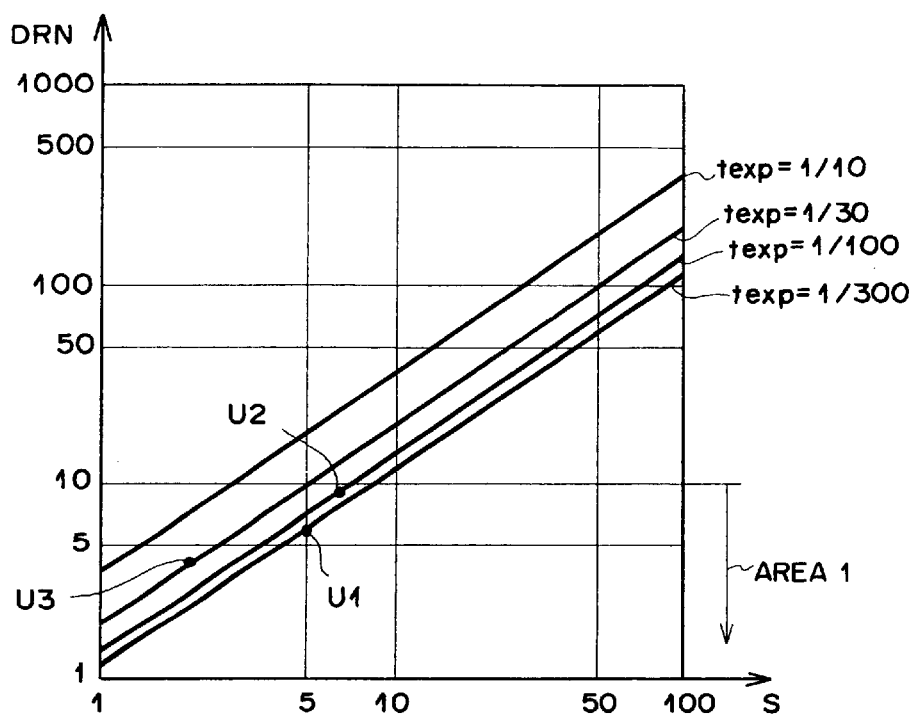
F I G. 5
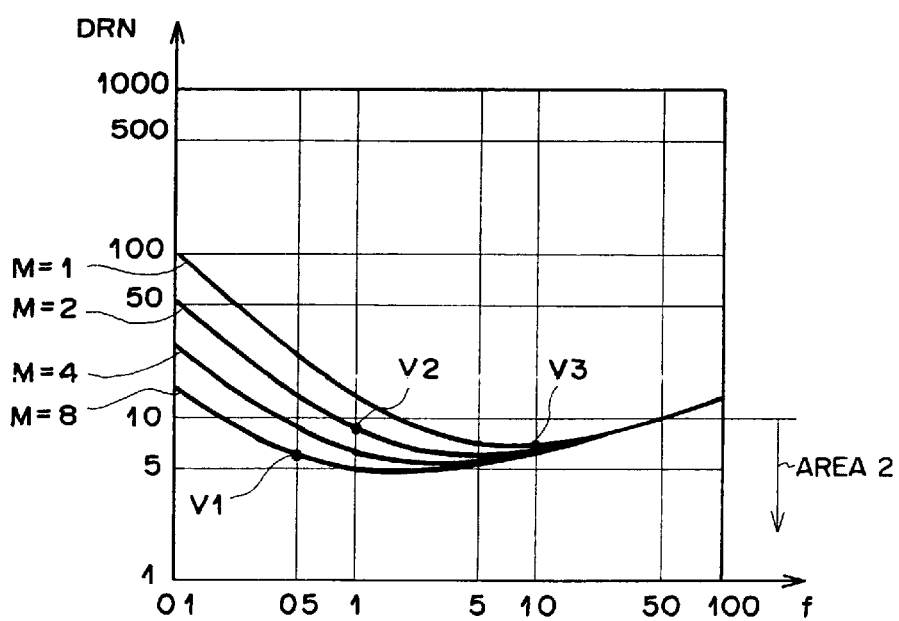

F I G . 10
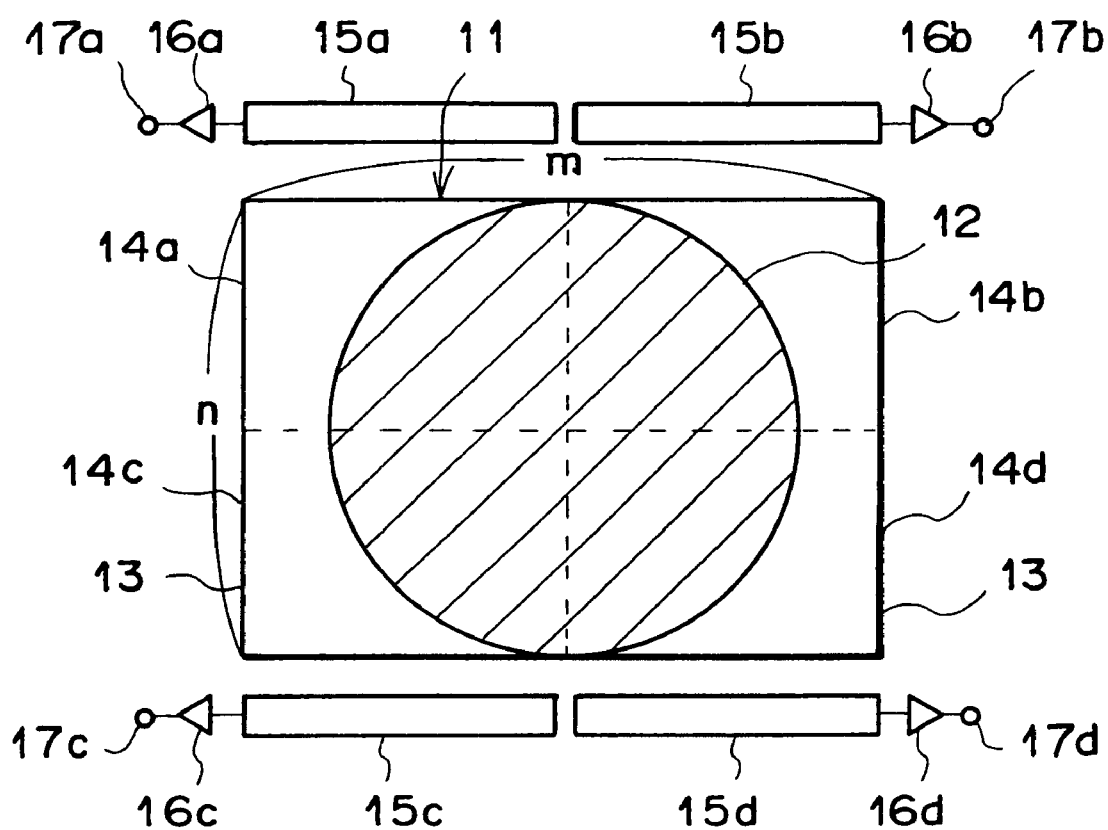

F I G. 11
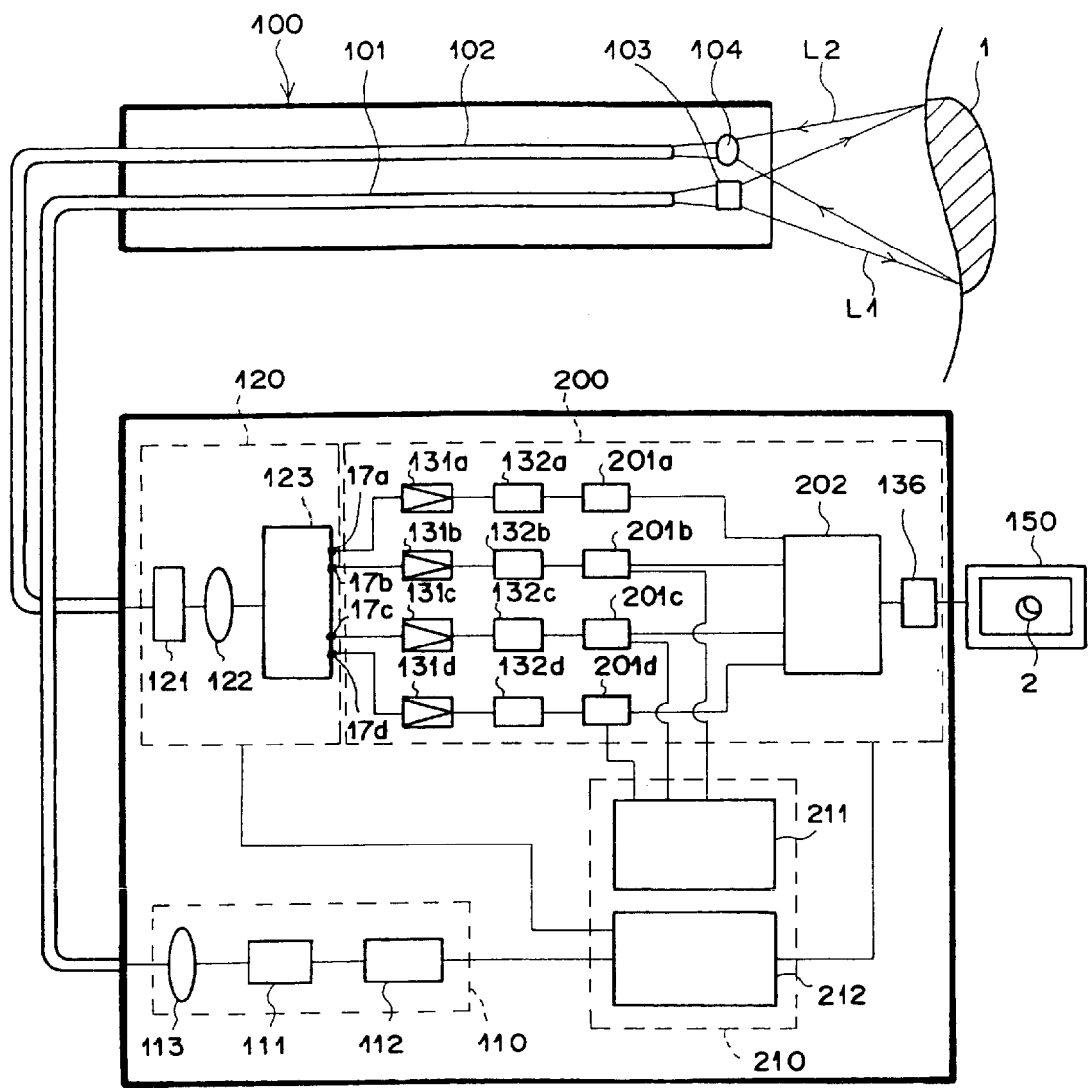

F I G . 12
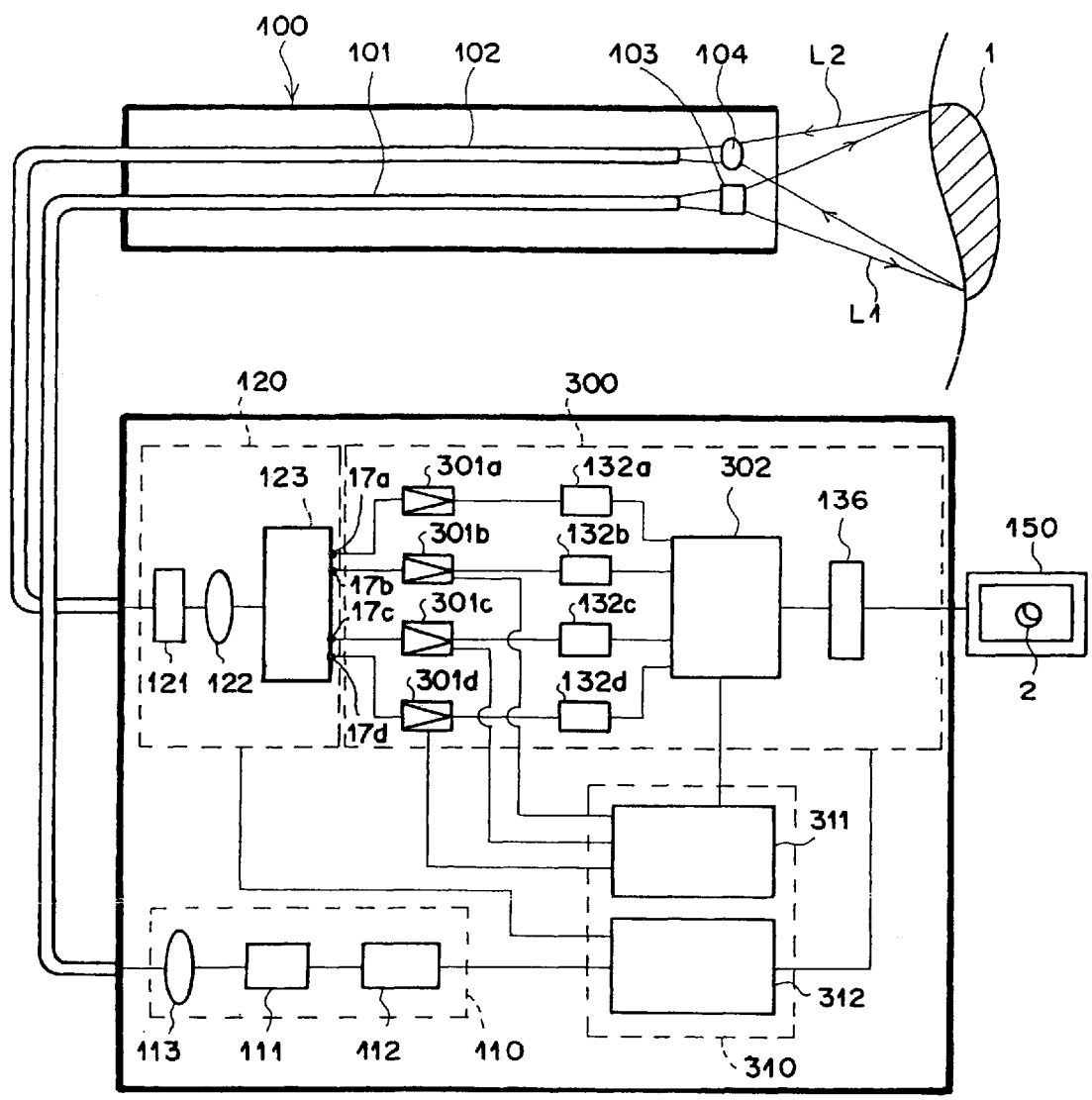

METHOD AND APPARATUS FOR ACQUIRING FLUORESCENCE IMAGES

BACKGROUND OF THE INVENTION

1. Field of the Invention

This invention relates to a method and apparatus for acquiring a fluorescence image, wherein intrinsic fluorescence, which is produced from living body tissues when the living body tissues are exposed to excitation light, is acquired as an image. This invention also relates to a fluorescence imaging apparatus for imaging fluorescence, which is produced from a measuring site when the measuring site is exposed to excitation light.

2. Description of the Related Art

Research has heretofore been conducted with respect to techniques, wherein intrinsic fluorescence, which is produced by an intrinsic dye in living body tissues when excitation light is irradiated to the living body tissues, is detected as an image, the image having been formed with the intrinsic fluorescence is analyzed, and a change in tissue condition of the living body tissues due to various kinds of diseases is discriminated in accordance with the results of the analysis.

The intrinsic fluorescence produced from the living body tissues is weak, and image sensors having a high sensitivity have heretofore been utilized for detecting the weak intrinsic fluorescence as an image. For example, in order for the intrinsic fluorescence to be imaged, there have heretofore been utilized high-sensitivity CCD (charge coupled device) image sensors, which are capable of performing pixel binning, i.e. processing for integrating signal charges of a plurality of pixels in each of CCD image sensor chips and reading the integrated signal charges. Also, electron multiplication types of image sensors, such as ICCD's, have heretofore been utilized to image the intrinsic fluorescence.

By way of example, the excitation light may be irradiated to living body tissues in the body cavity having a complicated shape, or the like, and a fluorescence image of the intrinsic fluorescence produced from the living body tissues may be acquired by utilizing an endoscope system. In such cases, it is desired that the intrinsic fluorescence produced from diseased tissues, such as cancerous tissues, which are located at a position (i.e., a remote point) spaced 50 mm apart from a leading end of a measuring probe of the endoscope system, be detected with a signal-to-noise ratio of at least 1.

However, in cases where the technique for performing the pixel binning is utilized, when the signal charges occurring in a plurality of pixels having received the intrinsic fluorescence are integrated in each of the CCD image sensor chips, electric charges occurring due to dark noise, which is contained in the signal charges accumulated in the pixels to be subjected to the pixel binning, are integrated together with the signal charges.

Therefore, since the intrinsic fluorescence produced from the cancerous tissues is weak, it often occurs that the number of electric charges occurring in each pixel due to the dark noise is larger than the number of electric charges occurring in each pixel due to the receiving of the intrinsic fluorescence. In such cases, even if the signal charges having been accumulated in the plurality of pixels are integrated with the pixel binning, the level of the signal representing the intrinsic fluorescence produced from the cancerous tissues will become lower than the level of the signal due to the dark noise. Therefore, the signal-to-noise ratio cannot be enhanced and will become lower than 1. Also, in cases where the electron multiplication types of image sensors are utilized, if the setting of the image sensor is not performed sufficiently accurately, it will often occur that the intrinsic fluorescence produced from the cancerous tissues located at the aforesaid remote point cannot be detected with a signal-to-noise ratio of at least 1 due to the occurrence of the dark noise and reading noise.

Further, it is desired that the intrinsic fluorescence produced from normal tissues, which are located at a position (i.e., a near point) spaced 5 mm apart from the leading end of the measuring probe of the endoscope system, be detected such that saturation may not be reached in a light receiving capacity of an imaging apparatus.

However, dynamic ranges of the electron multiplication types of image sensors, such as ICCD's, are narrower than the order of $10^1$. Therefore, if the setting of the image sensor is not performed sufficiently accurately, saturation will be reached in the light receiving capacity of the imaging apparatus. In cases where the technique for performing the pixel binning is utilized, as for the pixels in a region in which the intensity of received light is high, the number of pixels subjected to the pixel binning may be set at a small value. In this manner, the number of pixels subjected to the pixel binning may be set in accordance with the intensity of received light. However, in such cases, if the setting of the image sensor is not performed sufficiently accurately, the problems will occur in that saturation will be reached in the light receiving capacity of the imaging apparatus.

SUMMARY OF THE INVENTION

The primary object of the present invention is to provide a method of acquiring a fluorescence image, wherein an image of intrinsic fluorescence produced from a measuring site of living body tissues located at a remote point is capable of being acquired with a high signal-to-noise ratio.

Another object of the present invention is to provide a method of acquiring a fluorescence image, wherein an image of intrinsic fluorescence produced from a measuring site of living body tissues located at a near point is capable of being acquired such that saturation is not reached in light receiving capacity of an imaging apparatus.

A further object of the present invention is to provide an apparatus for carrying out the method of acquiring a fluorescence image.

A still further object of the present invention is to provide a fluorescence imaging apparatus, wherein reading noise is capable of being suppressed and a signal-to-noise ratio of a detected image is capable of being enhanced, such that adverse effects do not occur on displaying of a fluorescence image as a dynamic image.

The present invention provides a first method of acquiring a fluorescence image, comprising the steps of:

i) detecting intrinsic fluorescence, which has been produced from living body tissues when excitation light is irradiated to the living body tissues, with an image sensor, the excitation light causing the living body tissues to produce the intrinsic fluorescence, and ii) reading out the detected intrinsic fluorescence as an image, wherein the image is acquired by setting the image sensor such that a reading frequency, an area of one pixel, a total number of pixels, a number of pixels subjected to pixel binning, a number of reading ports, an exposure time, a quantum efficiency, an electron multiplication factor, and a sensor temperature of the image sensor satisfy the following condition formula:

$$RN+DN<0.22 \times P \times H \times G$$

The present invention also provides a second method of acquiring a fluorescence image, comprising the steps of:

i) detecting intrinsic fluorescence, which has been produced from living body tissues when excitation light is irradiated to the living body tissues, with an image sensor, the excitation light causing the living body tissues to produce the intrinsic fluorescence, and ii) reading out the detected intrinsic fluorescence as an image, wherein the image is acquired by setting the image sensor such that a reading frequency, an area of one pixel, a total number of pixels, a number of pixels subjected to pixel binning, a number of reading ports, an exposure time, a quantum efficiency, an electron multiplication factor, a sensor temperature, a floating diffusion capacity, and a full well capacity of the image sensor satisfy the following condition formulas:

$$(RN+DN) \times 1000 \times G < Fd$$

$$(RN+DN) \times 1000 \times G < Fw$$

The present invention further provides a first apparatus for acquiring a fluorescence image, comprising:

i) an image sensor for detecting intrinsic fluorescence, which has been produced from living body tissues when excitation light is irradiated to the living body tissues, the excitation light causing the living body tissues to produce the intrinsic fluorescence, and ii) read-out means for reading out the detected intrinsic fluorescence as an image, wherein the image sensor is set such that a reading frequency, an area of one pixel, a total number of pixels, a number of pixels subjected to pixel binning, a number of reading ports, an exposure time, a quantum efficiency, an electron multiplication factor, and a sensor temperature of the image sensor satisfy the following condition formula:

$$RN+DN<0.22 \times P \times H \times G$$

The present invention still further provides a second apparatus for acquiring a fluorescence image, comprising:

i) an image sensor for detecting intrinsic fluorescence, which has been produced from living body tissues when excitation light is irradiated to the living body tissues, the excitation light causing the living body tissues to produce the intrinsic fluorescence, and ii) read-out means for reading out the detected intrinsic fluorescence as an image, wherein the image sensor is set such that a reading frequency, an area of one pixel, a total number of pixels, a number of pixels subjected to pixel binning, a number of reading ports, an exposure time, a quantum efficiency, an electron multiplication factor, a sensor temperature, a floating diffusion capacity, and a full well capacity of the image sensor satisfy the following condition formulas:

$$(RN+DN) \times 1000 \times G < Fd$$

$$(RN+DN) \times 1000 \times G < Fw$$

In the first and second apparatuses for acquiring a fluorescence image in accordance with the present invention, the reading frequency may be set so as to satisfy the condition RN=DN.

Also, in the first and second apparatuses for acquiring a fluorescence image in accordance with the present invention, the image sensor may be a CCD type of image sensor or a MOS (metal oxide semiconductor) type of image sensor.

In the formulas described above, RN represents the number of electric charges occurring due to reading noise (which number is determined by the reading frequency and the area of one pixel), DN represents the number of electric charges occurring due to dark noise (which number is determined by the reading frequency, the area of one pixel, the total number of pixels, the number of pixels subjected to pixel binning, the number of reading ports, the exposure time, and the sensor temperature), P represents the irradiation output of the excitation light (in mW), H represents the quantum efficiency of the image sensor, G represents the electron multiplication factor of the image sensor, Fd represents the number of electric charges corresponding to the floating diffusion capacity, and Fw represents the number of electric charges corresponding to the full well capacity.

Also, RN and DN may be represented by the formulas shown below.

$$RN=0.17S^{0.777} \times f^{1/2}$$

$$DN=(\text{tread}+t\text{exp}) \times S \times n \times e^{d(T)}$$

$$\text{tread}=(N/n)/(f \times 10^6 \times M)+\{(n-1) \times (N/n)\}/(f \times 10^7 \times M)$$

$$d(T)=4.1913 \times 10^{-6} \times (273+T)^3 - 3.8015 \times 10^{-3} \times (273+T)^2 + 1.2197 \times (273+T) - 136$$

in which S represents the area of one pixel (in $\mu m^2$), f represents the reading frequency (in megapixel/sec), N represents the total number of pixels, n represents the number of pixels subjected to pixel binning, M represents the number of reading ports, texp represents the exposure time (in sec), and T represents the temperature of the image sensor (in °C.).

In the first and second methods of acquiring a fluorescence image in accordance with the present invention and the first and second apparatuses for acquiring a fluorescence image in accordance with the present invention, the image may be acquired as images, which are acquired successively for every 1/30 second per image frame as in ordinary cases. Alternatively, the image may be acquired as images, which are acquired successively, for example, for every 1/10 second per image frame such that, even if the motion of the detected images cannot be seen as a smooth motion, the measuring site is capable of being seen successively.

The term "number of electric charges corresponding to a capacity" as used herein means the value obtained by converting each of the floating diffusion capacity Fd and the full well capacity Fw into the number of electric charges in order to true up the units in the aforesaid formulas as the number of electric charges.

The first and second methods of acquiring a fluorescence image in accordance with the present invention may be combined with each other. Also, first and second apparatuses for acquiring a fluorescence image in accordance with the present invention may be combined with each other. Specifically, the image may be acquired by setting the image sensor such that the reading frequency, the area of one pixel, the total number of pixels, the number of pixels subjected to pixel binning, the number of reading ports, the exposure time, the quantum efficiency, the electron multiplication factor, the sensor temperature, the floating diffusion capacity, and the full well capacity of the image sensor satisfy the three condition formulas shown above, i.e. the following condition formulas:

$$RN+DN<0.22 \times P \times H \times G$$

$$(RN+DN) \times 1000 \times G < Fd$$

$$(RN+DN) \times 1000 \times G < Fw$$

The present invention also provides a fluorescence imaging apparatus, comprising:
i) irradiation means for irradiating excitation light to a measuring site, the excitation light causing the measuring site to produce fluorescence, and
ii) imaging means for detecting the fluorescence, which has been produced from the measuring site, the imaging means being provided with an imaging surface, which comprises a plurality of pixels arrayed in a two-dimensional form,
wherein the imaging means is provided with a plurality of output ports.

In the fluorescence imaging apparatus in accordance with the present invention, the imaging means may be one of various types of means provided with the imaging surface, which comprises a plurality of pixels arrayed in a two-dimensional form. For example, the imaging means may be an ordinary CCD image sensor, a MOS type of image sensor, a back surface incidence type of image sensor which is capable of performing high-sensitivity imaging, or a multiplication type of image sensor combined with multiplication means.

The fluorescence imaging apparatus in accordance with the present invention should preferably be modified such that the imaging surface is divided into N number of imaging blocks, where N is at least 2,
each of the output ports is provided for one of the N number of imaging blocks, and
the fluorescence imaging apparatus further comprises:
composing means for combining image signals, which have been outputted from the output ports, to form an image signal representing one image,
correction value calculating means for calculating correction values in accordance with variations in output characteristics among N number of output channels, which extend from the N number of imaging blocks to the composing means,
correction means for performing compensation for the variations in output characteristics, and
correction value setting means for setting the correction values in the correction means.

In such cases, the correction means should preferably be constituted of signal transforming means, which stores offset values and tone curve correction values.

Also, the fluorescence imaging apparatus in accordance with the present invention, wherein the correction means is constituted of the signal transforming means, should preferably be modified such that the imaging surface of the imaging means is constituted of an image exposure region and non-exposure regions,
each of the imaging blocks contains one of the non-exposure regions,
the correction value calculating means calculates the offset values, which act as the correction values, from image signals having been detected in a state, in which light impinges upon the imaging surface of the imaging means, and having been outputted through the respective output channels, the offset values being calculated such that signal intensities of image signals, which have been detected respectively in the non-exposure regions of the imaging blocks, take approximately identical values, and the correction value calculating means calculates the tone curve correction values, which act as the correction values, from the image signals having been detected in the state, in which light impinges upon the imaging surface of the imaging means, and having been outputted through the respective output channels, the tone curve correction values being calculated such that signal intensities of image signals, which have been detected respectively at adjacent ends of the imaging blocks that are adjacent to each other, take approximately identical values.

Further, the fluorescence imaging apparatus in accordance with the present invention, wherein the correction means is constituted of the signal transforming means, may be modified such that the correction value calculating means calculates the offset values, which act as the correction values, from image signals having been detected in a state, in which light is blocked from impinging upon the imaging surface of the imaging means, and having been outputted through the respective output channels, the offset values being calculated such that signal intensities of image signals, which have been detected respectively in the imaging blocks, take approximately identical values, and the correction value calculating means calculates the tone curve correction values, which act as the correction values, from image signals having been detected in a state, in which light impinges upon the imaging surface of the imaging means, and having been outputted through the respective output channels, the tone curve correction values being calculated such that signal intensities of image signals, which have been detected respectively at adjacent ends of the imaging blocks that are adjacent to each other, take approximately identical values.

Furthermore, in the fluorescence imaging apparatus in accordance with the present invention, the correction means may be constituted of amplification means, in which offset values and gains are capable of being adjusted.

Also, the fluorescence imaging apparatus in accordance with the present invention, wherein the correction means is constituted of the amplification means, should preferably be modified such that the imaging surface of the imaging means is constituted of an image exposure region and non-exposure regions,
each of the imaging blocks contains one of the non-exposure regions,
the correction value calculating means calculates the offset values, which act as the correction values, from image signals having been detected in a state, in which light impinges upon the imaging surface of the imaging means, and having been outputted through the respective output channels, the offset values being calculated such that signal intensities of image signals, which have been detected respectively in the non-exposure regions of the imaging blocks, take approximately identical values, and the correction value calculating means calculates gain adjustment values, which act as the correction values, from the image signals having been detected in the state, in which light impinges upon the imaging surface of the imaging means, and having been outputted through the respective output channels, the gain adjustment values being calculated such that signal intensities of image signals, which have been detected respectively at adjacent ends of the imaging blocks that are adjacent to each other, take approximately identical values.

Further, the fluorescence imaging apparatus in accordance with the present invention, wherein the correction means is constituted of the amplification means, may be modified such that the correction value calculating means calculates the offset values, which act as the correction values, from image signals having been detected in a state, in which light is blocked from impinging upon the imaging surface of the imaging means, and having been outputted through the respective output channels, the offset values being calculated such that signal intensities of image signals, which have been detected respectively in the imaging blocks, take approximately identical values, and the correction value calculating means calculates the gain adjustment values, which act as the correction values, from image signals having been detected in a state, in which light impinges upon the imaging surface of the imaging means, and having been outputted through the respective output channels, the gain adjustment values being calculated such that signal intensities of image signals, which have been detected respectively at adjacent ends of the imaging blocks that are adjacent to each other, take approximately identical values.

Furthermore, the fluorescence imaging apparatus in accordance with the present invention should preferably be modified such that the imaging surface of the imaging means is constituted of an image exposure region and non-exposure regions, the fluorescence imaging apparatus further comprises re-setting judgment means for making a judgment for each imaging operation and as to whether re-setting of the correction values is to be or is not to be performed, the judgment being made in accordance with the presence or absence of a change in signal intensity of an image signal, which has been detected in one of the non-exposure regions, the correction value calculating means operates such that, in cases where it has been judged by the re-setting judgment means that the re-setting of the correction values is to be performed, the correction value calculating means calculates new correction values, and the correction value setting means sets the new correction values, which have been calculated by the correction value calculating means, as the correction values in the correction means.

As described above, the judgment as to whether the re-setting of the correction values is to be or is not to be performed is made in accordance with the presence or absence of a change in signal intensity of an image signal, which has been detected in one of the non-exposure regions. For example, in cases where a change occurs in a mean value of signal intensities of the image signal, which has been detected in one of the non-exposure regions, or in cases where a change occurs in the signal intensity corresponding to a predetermined site, or the like, it is judged that the re-setting of the correction values is to be performed. In cases where such a change does not occur, it is judged that the correction values are not to be altered.

Also, the fluorescence imaging apparatus in accordance with the present invention may be modified such that the imaging surface is divided into N number of imaging blocks, where N is at least 2, each of the output ports is provided for one of the N number of imaging blocks, and the fluorescence imaging apparatus further comprises:
composing means for combining image signals, which have been outputted from the output ports, to form an image signal representing one image, correction value storing means for storing correction values for compensation for variations in output characteristics, the correction values having been calculated in accordance with the variations in output characteristics among N number of output channels, which extend from the N number of imaging blocks to the composing means, correction means for performing compensation for the variations in output characteristics, and correction value setting means for setting the correction values in the correction means.

In such cases, the correction means may be constituted of signal transforming means, which stores offset values and tone curve correction values. In such cases, the correction value storing means should preferably store the offset values and the tone curve correction values as the correction values.

Alternatively, the correction means may be constituted of amplification means, in which offset values and gains are capable of being adjusted. In such cases, the correction value storing means should preferably store the offset values and gain adjustment values as the correction values.

The fluorescence imaging apparatus in accordance with the present invention, wherein the correction value storing means is employed, should preferably be modified such that the correction value storing means stores signal intensity or a mean value of signal intensities of an image signal having been detected in a state, in which light is blocked from impinging upon the imaging surface of the imaging means, and corresponding correction values, the fluorescence imaging apparatus further comprises re-setting judgment means for making a judgment for each imaging operation and as to whether re-setting of the correction values is to be or is not to be performed, the judgment being made in accordance with the presence or absence of a change in signal intensity or a mean value of signal intensities of an image signal having been detected in a state, in which light is blocked from impinging upon the imaging surface of the imaging means, and the correction value setting means operates such that, in cases where it has been judged by the re-setting judgment means that the re-setting of the correction values is to be performed, the correction value setting means reads the correction values, which correspond to the signal intensity or the mean value of signal intensities of the image signal associated with the judgment in that the re-setting of the correction values is to be performed, from among the correction values having been stored in the correction value storing means and sets the correction values, which have thus been read from the correction value storing means, as the correction values in the correction means.

Also, the fluorescence imaging apparatus in accordance with the present invention, wherein the correction value storing means is employed, should preferably be modified such that the imaging surface of the imaging means is constituted of an image exposure region and non-exposure regions, the correction value storing means stores signal intensity or a mean value of signal intensities of an image signal, which has been detected in one of the non-exposure regions, and corresponding correction values, the fluorescence imaging apparatus further comprises re-setting judgment means for making a judgment for each imaging operation and as to whether re-setting of the correction values is to be or is not to be performed, the judgment being made in accordance with the presence or absence of a change in signal intensity or a mean value of signal intensities of an image signal, which has been detected in one of the non-exposure regions, and the correction value setting means operates such that, in cases where it has been judged by the re-setting judgment means that the re-setting of the correction values is to be performed, the correction value setting means reads the correction values, which correspond to the signal intensity or the mean value of signal intensities of the image signal associated with the judgment in that the re-setting of the correction values is to be performed, from among the correction values having been stored in the correction value storing means and sets the correction values, which have thus been read from the correction value storing means, as the correction values in the correction means.

Further, the fluorescence imaging apparatus in accordance with the present invention, wherein the correction value storing means is employed, should preferably be modified such that the correction value storing means stores information representing a temperature in the vicinity of the imaging means and corresponding correction values, which have been calculated by the correction value calculating means, the fluorescence imaging apparatus further comprises:

temperature detecting means for detecting the temperature in the vicinity of the imaging means, and re-setting judgment means for making a judgment for each imaging operation and as to whether re-setting of the correction values is to be or is not to be performed, the judgment being made in accordance with the presence or absence of a change in temperature in the vicinity of the imaging means, and the correction value setting means operates such that, in cases where it has been judged by the re-setting judgment means that the re-setting of the correction values is to be performed, the correction value setting means reads the correction values, which correspond to the temperature in the vicinity of time imaging means associated with the judgment in that the re-setting of the correction values is to be performed, from among the correction values having been stored in the correction value storing means and sets the correction values, which have thus been read from the correction value storing means, as the correction values in the correction means.

In the fluorescence imaging apparatus in accordance with the present invention, the value of N should preferably be at most 64, and should more preferably be at most 8.

With the first method of acquiring a fluorescence image and the first apparatus for acquiring a fluorescence image in accordance with the present invention, in which the intrinsic fluorescence having been detected by the image sensor is acquired as the image, the image sensor is set so as to satisfy the condition formula:

$$RN+DN<0.22\times P\times H\times G$$

Therefore, the number of electric charges occurring in the imaging apparatus due to dark noise and reading noise is restricted to be smaller than the number of electric charges occurring in the imaging apparatus due to the intrinsic fluorescence produced from the measuring site. Accordingly, the fluorescence image is capable of being acquired with a high signal-to-noise ratio.

With the second method of acquiring a fluorescence image and the second apparatus for acquiring a fluorescence image in accordance with the present invention, in which the intrinsic fluorescence having been detected by the image sensor is acquired as the image, the image sensor is set so as to satisfy the condition formulas:

$$(RN+DN)\times 1000\times G<Fd$$

$$(RN+DN)\times 1000\times G<Fw$$

Therefore, the floating diffusion capacity and the full well capacity of the imaging apparatus are capable of taking sufficiently large values in comparison with the number of electric charges occurring in the imaging apparatus due to dark noise and reading noise. As a result, the fluorescence image is capable of being acquired such that saturation is not reached in the light receiving capacity of the imaging apparatus.

With the first and second apparatuses for acquiring a fluorescence image in accordance with the present invention, wherein the reading frequency f of the image sensor is set so as to satisfy the condition RN=DN, the sum of the number of electric charges occurring due to dark noise and the number of electric charges occurring due to reading noise is capable of being minimized.

Also, with the first and second apparatuses for acquiring a fluorescence image in accordance with the present invention, wherein the image sensor is the CCD type of image sensor or the MOS type of image sensor, the space for the image sensor is capable of being kept small.

With the fluorescence imaging apparatus in accordance with the present invention, wherein the imaging means is provided with a plurality of output ports, the number of pixels allocated to one output port is capable of being reduced to one-half or less in comparison with the cases where the imaging means is provided with only a single output port. Therefore, even if the reading frequency is set at a low value, signal charges of all pixels are capable of being read within the reading time. Accordingly, reading noise is capable of being suppressed and the signal-to-noise ratio of the detected image is capable of being enhanced, such that adverse effects do not occur on displaying of the fluorescence image as a dynamic image.

In cases where the imaging surface is divided into N number of imaging blocks, where N is at least 2, and each of the output ports is provided for one of the N number of imaging blocks, the imaging means provided with a plurality of output ports can be formed easily. However, in such cases, the uniformity of the characteristics of the output system, which uniformity an image sensor naturally has, is lost. Specifically, variations in output characteristics will occur among N number of output channels, which extend from the N number of imaging blocks to the composing means for composing an image signal representing one image from the image signals having been outputted from the output ports, and division line patterns will appear in the formed image. However, with the fluorescence imaging apparatus in accordance with the present invention, the correction values are calculated in accordance with variations in output characteristics among N number of output channels, which extend from the N number of imaging blocks to the composing means. Also, the calculated correction values are set in the correction means for performing compensation for the variations in output characteristics. Therefore, the variations in output characteristics are capable of being compensated for, and the problems are capable of being prevented from occurring in that division line patterns appear in the formed image.

With the fluorescence imaging apparatus in accordance with the present invention, wherein the correction means is constituted of the signal transforming means, which stores the offset values and the tone curve correction values, the compensation for the output characteristics is capable of being performed easily.

With the fluorescence imaging apparatus in accordance with the present invention, wherein each of the imaging blocks contains one of the non-exposure regions, the offset values and the tone curve correction values, which act as the correction values, are capable of being calculated from the image signals having been detected in the state, in which light impinges; upon the imaging surface of the imaging means. Therefore, the calculations of the correction values are capable of being made such that the ordinary imaging operation is not obstructed.

With the fluorescence imaging apparatus in accordance with the present invention, the offset values, which act as the correction values, may be calculated from the image signals having been detected in the state, in which light is blocked from impinging upon the imaging surface of the imaging means, and the tone curve correction values, which act as the correction values, may be calculated from the image signals having been detected in the state, in which light impinges upon the imaging surface of the imaging means. In such cases, all of the imaging blocks need not necessarily contain the non-exposure regions, and therefore the flexibility in manner of division of the imaging blocks is capable of being enhanced.

With the fluorescence imaging apparatus in accordance with the present invention, wherein the correction means is constituted of the amplification means, in which the offset values and the gains are capable of being adjusted, amplification means, which has heretofore been provided in a signal processing circuit, can be utilized as the correction means. Therefore, new circuit parts need not be provided, and the production cost is capable of being kept low.

Also, with the fluorescence imaging apparatus in accordance with the present invention, wherein each of the imaging blocks contains one of the non-exposure regions, the offset values and the gain adjustment values, which act as the correction values, are capable of being calculated from the image signals having been detected in the state, in which light impinges upon the imaging surface of the imaging means. Therefore, the calculations of the correction values are capable of being made such that the ordinary imaging operation is not obstructed.

With the fluorescence imaging apparatus in accordance with the present invention, the offset values, which act as the correction values, may be calculated from the image signals having been detected in the state, in which light is blocked from impinging upon the imaging surface of the imaging means, and the gain adjustment values, which act as the correction values, may be calculated from the image signals having been detected in the state, in which light impinges upon the imaging surface of the imaging means. In such cases, all of the imaging blocks need not necessarily contain the non-exposure regions, and therefore the flexibility in manner of division of the imaging blocks is capable of being enhanced.

It has been known that the output characteristics of the output channels vary for different ambient temperatures.

Also, the image signal, which has been detected in the non-exposure region of the imaging surface of the imaging means, is the one primarily due to dark current and varies for different ambient temperatures. Therefore, if no change occurs in signal intensity of the image signal, which has been detected in the non-exposure region of the imaging surface of the imaging means, it can be regarded that no change occurs in output characteristics. Accordingly, a change in signal intensity of the image signal, which has been detected in one of the non-exposure regions, may be investigated for each imaging operation. In cases where no change in signal intensity occurs, it may be regarded that no change occurs in output characteristics, and corrections may be made by utilizing the correction values, which have already been set in the correction means. In this manner, the number of times of calculations of new correction values is capable of being reduced, and the processing time required to make the compensation for the output characteristics is capable of being kept short.

With the fluorescence imaging apparatus in accordance with the present invention, wherein the correction value storing means is employed, the correction values, which have been calculated in accordance with the variations in output characteristics among N number of output channels extending from the N number of imaging blocks to the composing means and which have been stored in the correction value storing means, may be set in the correction means for performing compensation for the variations in output characteristics. Therefore, the number of pixels allocated to one output port is capable of being reduced to a value smaller than in cases where the imaging means is provided with only a single output port. Therefore, even if the reading frequency is set at a low value, signal charges of all pixels are capable of being read within the reading time. Accordingly, reading noise is capable of being suppressed and the signal-to-noise ratio of the detected image is capable of being enhanced, such that adverse effects do not occur on displaying of the fluorescence image as a dynamic image. Also, the variations in output characteristics are capable of being compensated for, and the problems are capable of being prevented from occurring in that division line patterns appear in the formed image, such that adverse effects do not occur on displaying of the fluorescence image as a dynamic image.

With the fluorescence imaging apparatus in accordance with the present invention, wherein the correction value storing means is employed, the correction means may be constituted of the signal transforming means, which stores the offset values and the tone curve correction values, and the correction value storing means may store the offset values and the tone curve correction values as the correction values. In such cases, the compensation for the output characteristics is capable of being made easily.

With the fluorescence imaging apparatus in accordance with the present invention, wherein the correction means is constituted of the amplification means, in which the offset values and the gains are capable of being adjusted, and the correction value storing means stores the offset values and gain adjustment values as the correction values, amplification means, which has heretofore been provided in a signal processing circuit, can be utilized as the correction means. Therefore, new circuit parts need not be provided, and the production cost is capable of being kept low.

With the fluorescence imaging apparatus in accordance with the present invention, wherein the correction value storing means is employed, the correction value storing means may store the signal intensity or the mean value of signal intensities of the image signal having been detected in the state, in which light is blocked from impinging upon the imaging surface of the imaging means, and the corresponding correction values. Also, for each imaging operation, a change of the signal intensity or the mean value of signal intensities of the image signal having been detected in the state, in which light is blocked from impinging upon the imaging surface of the imaging means, may be investigated. In cases where a change of the signal intensity or the mean value of signal intensities of the image signal occurs, the correction values, which correspond to the signal intensity or the mean value of signal intensities of the image signal associated with the judgment in that the re-setting of the correction values is to be performed, may be read from among the correction values having been stored in the correction value storing means and may be set as the correction values in the correction means. In such cases, the processing for calculating the correction values is capable of being omitted, and the processing time required to make the compensation for the output characteristics is capable of being kept short.

With the fluorescence imaging apparatus in accordance with the present invention, wherein the correction value storing means is employed, the correction value storing means may store the signal intensity or the mean value of signal intensities of the image signal, which has been detected in one of the non-exposure regions, and corresponding correction values. Also, for each imaging operation, a change of the signal intensity or the mean value of signal intensities of the image signal, which has been detected in one of the non-exposure regions, may be investigated. In cases where a change of the signal intensity or the mean value of signal intensities of the image signal occurs, the correction values, which correspond to the signal intensity or the mean value of signal intensities of the image signal associated with the judgment in that the re-setting of the correction values is to be performed, may be read from among the correction values having been stored in the correction value storing means and may be set as the correction values in the correction means. In such cases, the processing for calculating the correction values is capable of being omitted, and the processing time required to make the compensation for the output characteristics is capable of being kept short. Also, the change of the signal intensity or the mean value of signal intensities of the image signal, which has been detected in one of the non-exposure regions, can be detected by utilizing the ordinary imaging operation. Therefore, the processing for the compensation for the output characteristics is capable of being simplified.

With the fluorescence imaging apparatus in accordance with the present invention, wherein the correction value storing means is employed, the correction value storing means may store the information representing the temperature in the vicinity of the imaging means and the corresponding correction values, which have been calculated by the correction value calculating means, and the temperature detecting means for detecting the temperature in the vicinity of the imaging means may be provided. Also, for each imaging operation, a change in temperature in the vicinity of the imaging means may be investigated. In cases where a change in temperature occurs, the correction values, which correspond to the temperature in the vicinity of the imaging means associated with the judgment in that the re-setting of the correction values is to be performed, may be read from among the correction values having been stored in the correction value storing means and may be set as the correction values in the correction means. In such cases, the processing for calculating the correction values is capable of being omitted, and the processing time required to make the compensation for the output characteristics is capable of being kept short. Also, the acquisition and comparison of the temperature in the vicinity of the imaging means can be performed with simple processing. Therefore, the processing for the compensation for the output characteristics is capable of being simplified even further.

With the fluorescence imaging apparatus in accordance with the present invention, wherein the value of N, i.e. the number of division of the imaging surface, falls within the range of 2 to 64, the reading frequency is capable of being set at a low value, and reading noise is capable of being suppressed, such that peripheral circuits and the compensation processing may not become complicated. Also, in cases where the value of N, i.e. the number of division of the imaging surface, falls within the range of 2 to 8, the peripheral circuits and the compensation processing are capable of being simplified even further.

BRIEF DESCRIPTION OF THE DRAWINGS

FIG. 4 is a graph showing relationship between a total number of noise charges DRN and an area of one pixel S, FIG. 5 is a graph showing relationship between the total number of noise charges DRN and a reading frequency f, FIG. 10 is a schematic view showing part of a CCD image sensor employed in the endoscope system, in which the first embodiment of the fluorescence imaging apparatus in accordance with the present invention is employed, FIG. 11 is a schematic view showing an endoscope system, in which a second embodiment of the fluorescence imaging apparatus in accordance with the present invention is employed, FIG. 12 is a schematic view showing an endoscope system, in which a third embodiment of the fluorescence imaging apparatus in accordance with the present invention is employed.

DESCRIPTION OF THE PREFERRED EMBODIMENTS

The present invention will hereinbelow be described in further detail with reference to the accompanying drawings.

Figure 1:
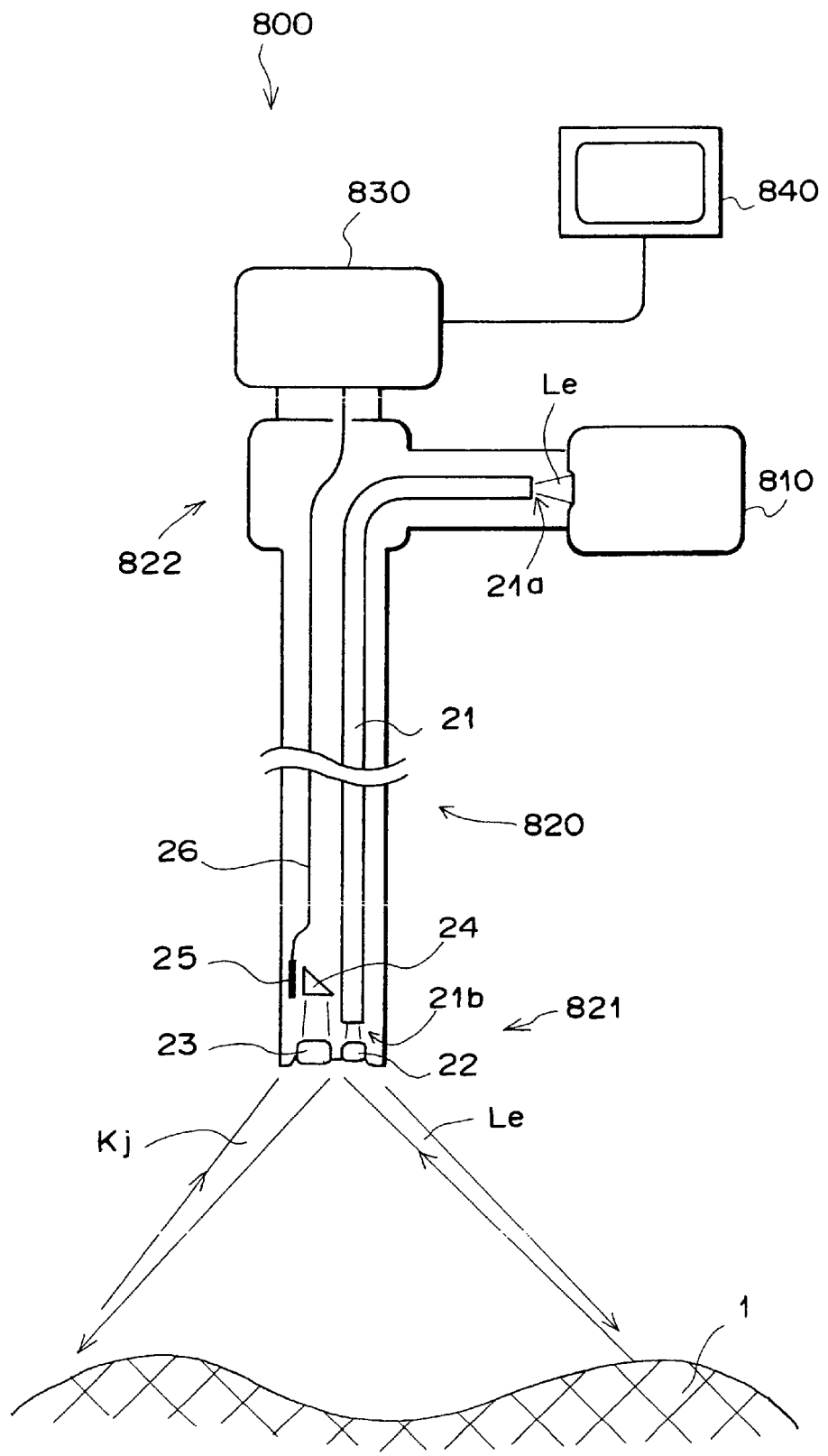
FIG. 1 is a schematic view showing a fluorescence endoscope system, in which an embodiment of the apparatus for acquiring a fluorescence image in accordance with the present invention is employed.

FIG. 1 is a schematic view showing a fluorescence endoscope system, in which an embodiment of the apparatus for acquiring a fluorescence image in accordance with the present invention is employed.

With reference to FIG. 1, a fluorescence endoscope system 800 comprises a light source unit 810 for producing excitation light Le having a wavelength of 410 nm. The fluorescence endoscope system 800 also comprises an endoscope unit 820 for receiving the excitation light Le from the light source unit. 810, irradiating the excitation light Le through an optical fiber 21 to living body tissues 1, imaging intrinsic fluorescence Kj, which has been produced from the living body tissues 1 when the excitation light Le is irradiated to the living body tissues 1, with an image sensor 25, and feeding out an image signal, which represents the image of the intrinsic fluorescence Kj, through a cable 26. The fluorescence endoscope system 800 further comprises an image signal read-out unit 830 for reading out the image signal from the endoscope unit 820, and transforming the image signal into a video signal. The fluorescence endoscope system 800 still further comprises a display device 840 for receiving the video signal from the image signal read-out unit 830, reproducing a visible image from the video signal, and displaying the visible image.

The endoscope unit 820 comprises an operating section 822, which is connected to the light source unit 810 and the image signal read-out unit 830. The endoscope unit 820 also comprises a measuring probe section 821. The measuring probe section 821 is provided with an irradiating lens 22 for irradiating the excitation light Le to the living body tissues 1, and an image forming lens 23 for forming the image of the living body tissues 1, which image is obtained with the intrinsic fluorescence Kj having been produced from the living body tissues 1, on the image sensor 25 via a prism 24. (The image of the living body tissues 1 obtained with the intrinsic fluorescence Kj will hereinbelow be referred to as the intrinsic fluorescence image Zj.) The optical fiber 21 and the cable 26 extend in the endoscope unit 820 from the operating section 822 to the measuring probe section 821. An excitation light. cut-off filter for blocking light having a wavelength of 410 nm is combined with a light receiving surface of the image sensor 25.

How the fluorescence endoscope system 800 operates will be described hereinbelow. The excitation light Le, which has bee produced by the light source unit 810, impinges upon an end face 21a of the optical fiber 21, is guided through the optical fiber 21, and emanates from an end face 21b of the optical fiber 21. The excitation light Le, which has emanated from the end face 21b, is irradiated from the irradiating lens 22 as excitation light having been diverged to an angle of approximately 120° and having an output of 100 mW. The intrinsic fluorescence image Zj of the intrinsic fluorescence Kj, which has been produced from the living body tissues 1 when the excitation light Le is irradiated to the living body tissues 1, passes through the image forming lens 23 and impinges upon the prism 24. The direction of the optical path of the intrinsic fluorescence image Zj is changed by the prism 24 by an angle of approximately 90°, and the intrinsic fluorescence image Zj is formed on the image sensor 25. At this time, the excitation light Le is blocked by the excitation light cut-off filter, which is combined with the light receiving surface of the image sensor 25, and therefore only the intrinsic fluorescence image Zj is received by the image sensor 25. The intrinsic fluorescence image Zj having been formed on the image sensor 25 is detected by the image sensor 25 and converted into an electric image signal. The thus obtained image signal is transmitted through the cable 26 and read out by the image signal read-out unit 830. The image signal is transformed by the image signal read-out unit 830 into the video signal. The video signal is fed from the image signal read-out unit 830 into the display device 840. The display device 840 reproduces a visible image from the video signal and displays the visible image.

In the first embodiment of the apparatus for acquiring a fluorescence image in accordance with the present invention, conditions are set in the manner described below in order for the intrinsic fluorescence Kj, which has been produced from a measuring range extending from a near point to a remote point, to be acquired with a sufficiently high signal-to-noise ratio, such that saturation may not be reached in the light receiving capacity of the imaging apparatus.

Specifically, such that the intensity of the intrinsic fluorescence Kj, which has been produced from diseased tissues, such as cancerous tissues, located in a measuring region at a remote point, may be acquired with a signal-to-noise ratio of at least 1, the image sensor 25 is set in accordance with Formula (1) shown below.

$$RN+DN<0.22\times P\times H\times G \tag{1}$$

Also, in order for the intrinsic fluorescence Kj, which has been produced from a near point, to be acquired such that saturation may not be reached in the light receiving capacity of the imaging apparatus, the image sensor 25 is set in accordance with Formulas (2) and (3) shown below.

$$(RN+DN)\times 1000\times G<Fd \tag{2}$$

$$(RN+DN)\times 1000\times G<Fw \tag{3}$$

In the formulas described above, RN represents the number of electric charges occurring due to reading noise, DN represents the number of electric charges occurring due to dark noise (i.e., due to dark current), P represents the irradiation output of the excitation light (in mW), H represents the quantum efficiency of the image sensor, G represents the electron multiplication factor of the image sensor, Fd represents the number of electric charges corresponding to the floating diffusion capacity, and Fw represents the number of electric charges corresponding to the full well capacity.

Also, RN and DN may be represented by the formulas shown below.

$$RN=0.17 S^{0.777}\times f^{1/2}$$

$$DN=(tread+texp)\times S\times n\times e^{d(T)}$$

$$tread=(N/n)/(f\times 10^6 \times M)+\{(n-1)\times (N/n)\}/(f\times 10^7 \times M)$$

$$d(T)=4.1913\times 10^{-6}\times (273+T)^3-3.8015\times 10^{-3}\times (273+T)^2+1.2197\times (273+T)-136$$

in which S represents the area of one pixel (in $\mu m^2$), f represents the reading frequency (in megapixel/sec), N represents the total number of pixels, n represents the number of pixels subjected to pixel binning, M represents the number of reading ports, texp represents the exposure time (in sec), and T represents the temperature of the image sensor (in ° C.).

Figure 2:
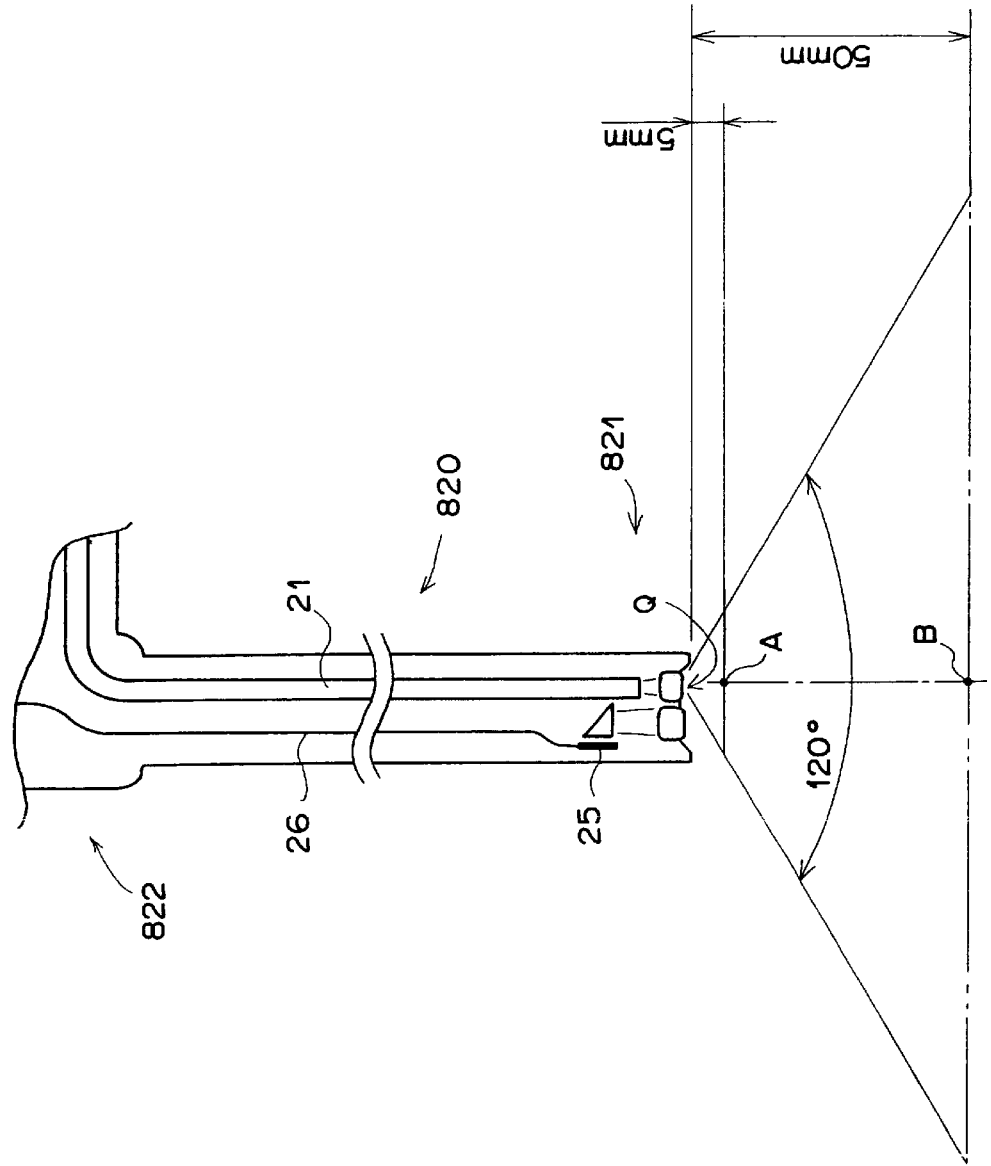
FIG. 2 is an explanatory view showing a range of irradiation of excitation light.

Firstly, how the right-hand side of Formula (1) is defined will be described hereinbelow. A first image acquisition requirement of the fluorescence endoscope is that the intrinsic fluorescence Kj, which is produced from the cancerous tissues located at a position 50 mm spaced apart from the leading end of the measuring probe section 821 when the excitation light Le having a wavelength of 410 nm is irradiated to the cancerous tissues, be detected with a signal-to-noise ratio of at least 1. Specifically, as illustrated in FIG. 2, it is required that, when the excitation light Le having an irradiation output of 100 mW is radiated out at a divergence angle of 120° from a radiating-out point Q of the irradiating lens 22, the intrinsic fluorescence Kj, which is produced from the cancerous tissues located at a position B 50 mm spaced apart from the radiating-out point Q, be acquired as an image with a signal-to-noise ratio of at least 1.

Figure 3:
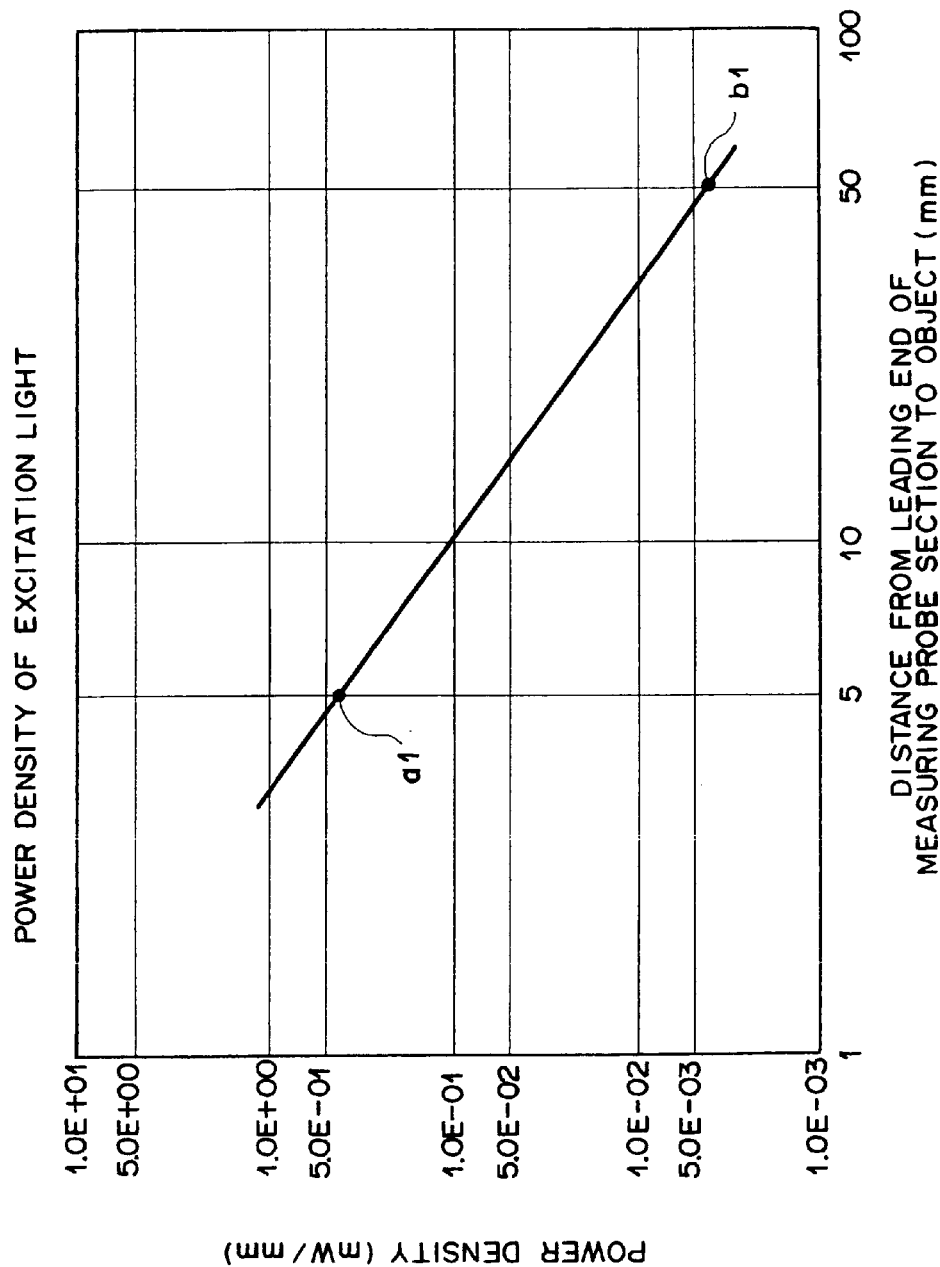
FIG. 3 is a graph showing relationship between a distance from a leading end of a measuring probe to an object and power density of excitation light.

As indicated by a point b1 in the bi-logarithmic graph of FIG. 3, the power density of the excitation light Le, which is irradiated to the position B with the setting described above, is equal to 0.004 (mW/mm$^2$). The image of the intrinsic fluorescence Kj, which is produced from the cancerous tissues when the cancerous tissues are exposed to the excitation light Le having the power density of 0.004 (mW/mm$^2$), may be formed on a pixel of the image sensor 25 by the image forming lens 23 and may be detected for an exposure time of $\frac{1}{30}$ second. In such cases, for example, if the quantum efficiency H and the electron multiplication factor G of the image sensor 25 are equal to 1 and the area of one pixel S is 10 $\mu$m$^2$, the number of electric charges accumulated at the pixel of the image sensor 25 will be equal to approximately 22. In order for the 22 electric charges to be read with a signal-to-noise ratio of at least 1, it is necessary for the number of electric charges constituting noise, which are read from the same pixel, to be restricted to a value smaller than 22.

In order for the setting described above to be generalized even further, in cases where the irradiation output P of the excitation light Le is 100 mW, and the quantum efficiency H and the electron multiplication factor G of the image sensor 25 are equal to 1, even if the area of one pixel S and the number of pixels subjected to pixel binning, which pixels are processed as being equivalent to one pixel, alter, the minimum number of the electric charges, which are read from one pixel (or the pixels processed as being equivalent to one pixel) with a signal-to-noise ratio of at least 1, may be fixedly assumed to be 22. Also, it is set such that the sum of the electric charges due to dark noise and reading noise occurring from one pixel (or the pixels processed as being equivalent to one pixel) becomes less than 22.

Also, with the setting described above being taken as reference setting, the irradiation output P of the excitation light Le, the quantum efficiency H of the image sensor 25, and the electron multiplication factor G of the image sensor 25 are taken as variables, and the minimum number of the electric charges occurring from one pixel (or the pixels processed as being equivalent to one pixel), which electric charges are to be read with a signal-to-noise ratio of at least 1, is calculated. The calculation is made with the formula:

$$22 \times (P/100) \times H \times G = 0.22 \times P \times H \times G \text{ (pieces)}$$

Therefore, the thus obtained formula is defined as the right-hand side of Formula (1).

Specifically, the irradiation output P is 100 mW, and image detection is performed with front exposure by utilizing the CCD image sensor. Also, the quantum efficiency H of the image sensor is H=0.4, and the electron multiplication factor G of the image sensor is G=1. Therefore, according to the conditions described above, the minimum setting number of the electric charges, which are accumulated in one pixel (or the pixels processed as being equivalent to one pixel), is 0.22×100×0.4×1=8.8. The minimum setting number, 8.8, of the electric charges, which are accumulated in one pixel (or the pixels processed as being equivalent to one pixel), will hereinbelow be rounded and simplified as being 10.

How the left-hand side of Formula (1) is defined will be described hereinbelow. In cases where the intrinsic fluorescence image Zj is detected with front exposure by utilizing the CCD image sensor in the manner described above, it is necessary that the sum of the number of the electric charges due to dark noise and the number of the electric charges due to reading noise, which electric charges occur from one pixel (or the pixels processed as being equivalent to one pixel), be restricted to a value smaller than 10. The setting for satisfying the requirement may be performed in various manners and may be performed in the manner described below.

For example, in cases where front exposure is performed by utilizing the CCD image sensor, it may be set such that T=20 (° C.), N=250,000 (pieces), n=16 (pieces), f=1 (megapixel/sec), and M=1 (port). Also, texp may be set stepwise to be $\frac{1}{10}$, $\frac{1}{30}$, $\frac{1}{100}$, and $\frac{1}{300}$ (sec), and the area of one pixel S may be set at various different values ranging from 1 to 100 ($\mu$m$^2$). In such cases, the relationship between the value of the area of one pixel S and the sum DN+RN of the number of the electric charges due to dark noise and the number of the electric charges due to reading noise is represented by the graph of FIG. 4. (The sum DN+RN will hereinbelow be referred to as the total number of noise charges DRN.) In FIG. 4, the area of one pixel S is plotted on the X axis, and the total number of noise charges DRN is plotted on the Y axis. As illustrated in FIG. 4, the range of the setting, with which the total number of noise charges DRN occurring from one pixel (or the pixels processed as being equivalent to one pixel) can be restricted to be smaller than 10 (pieces), is the range of Y<10, which is indicated as "Area 1." Specifically, for example, the setting may be performed with setting values such that DRN=6 (pieces) under the conditions of texp=$\frac{1}{300}$ (sec) and S=5 ($\mu$m$^2$) indicated at a point u1, setting values such that DRN=9 (pieces) under the conditions of texp=$\frac{1}{100}$ (sec) and S=6.5 ($\mu$m$^2$) indicated at a point u2, or setting values such that DRN=4 (pieces) under the conditions of texp=$\frac{1}{30}$ (sec) and S=2 ($\mu$m$^2$) indicated at a point u3.

Also, as a different example, in cases where front exposure is performed by utilizing the CCD image sensor, it may be set such that T=20 (° C.), N=250,000 (pieces), n=16 (pieces), M=1, 2, 4, and 8 (port), S=10 ($\mu$m$^2$), and texp=$\frac{1}{100}$ (sec). Also, the reading frequency f may be set at various different values ranging from f=0.1 (megapixel/sec) to f=100 (megapixel/sec). In such cases, the relationship between the value of the reading frequency f and the total number of noise charges DRN is represented by the graph of FIG. 5. In FIG. 5, the reading frequency f is plotted on the X axis, and the total number of noise charges DRN is plotted on the Y axis. As illustrated in FIG. 5, the range of the setting, with which the total number of noise charges DRN occurring from one pixel (or the pixels processed as being equivalent to one pixel) can be restricted to be smaller than 10 (pieces), is the range of Y<10, which is indicated as "Area 2." Specifically, for example, the setting may be performed with setting values such that DRN=6 (pieces) under the conditions of M=8 (ports) and f=5 (megapixel/sec) indicated at a point v1, setting values such that DRN=9 (pieces) under the conditions of M=2 (ports) and f=1 (megapixel/sec) indicated at a point v2, or setting values such that DRN=7 (pieces) under the conditions of M=1 (port) and f=10 (megapixel/sec) indicated at a point v3.

Figure 6:
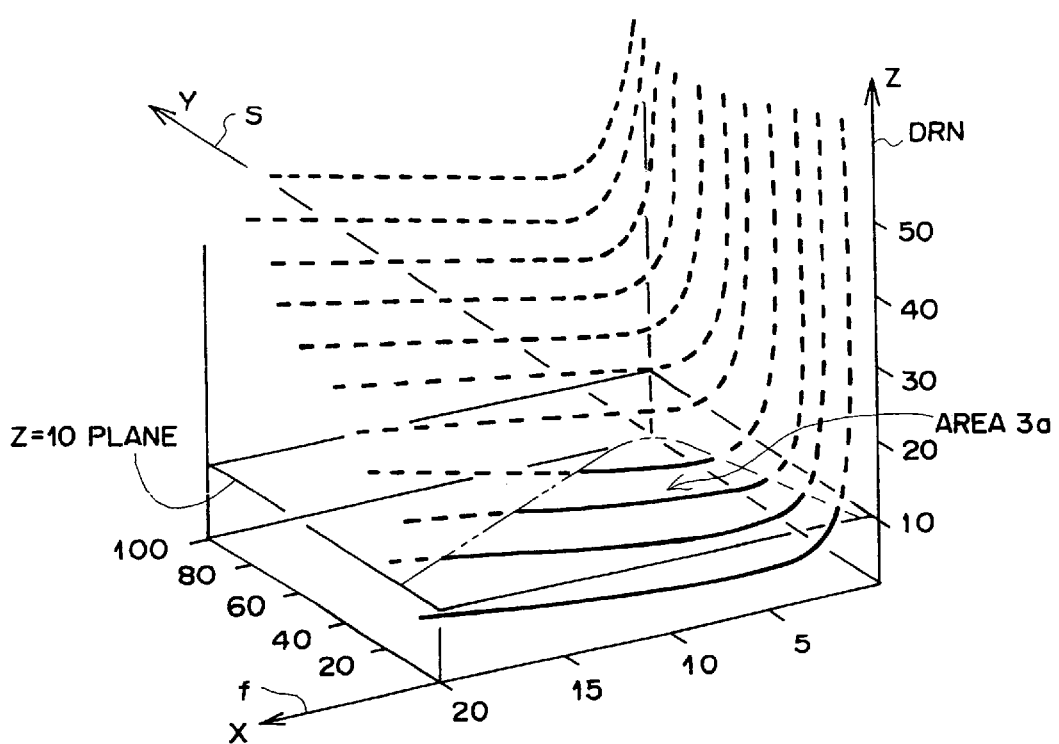
FIG. 6 is a graph showing relationship among the total number of noise charges DRN, the reading frequency f, and the area of one pixel S.
Figure 7:
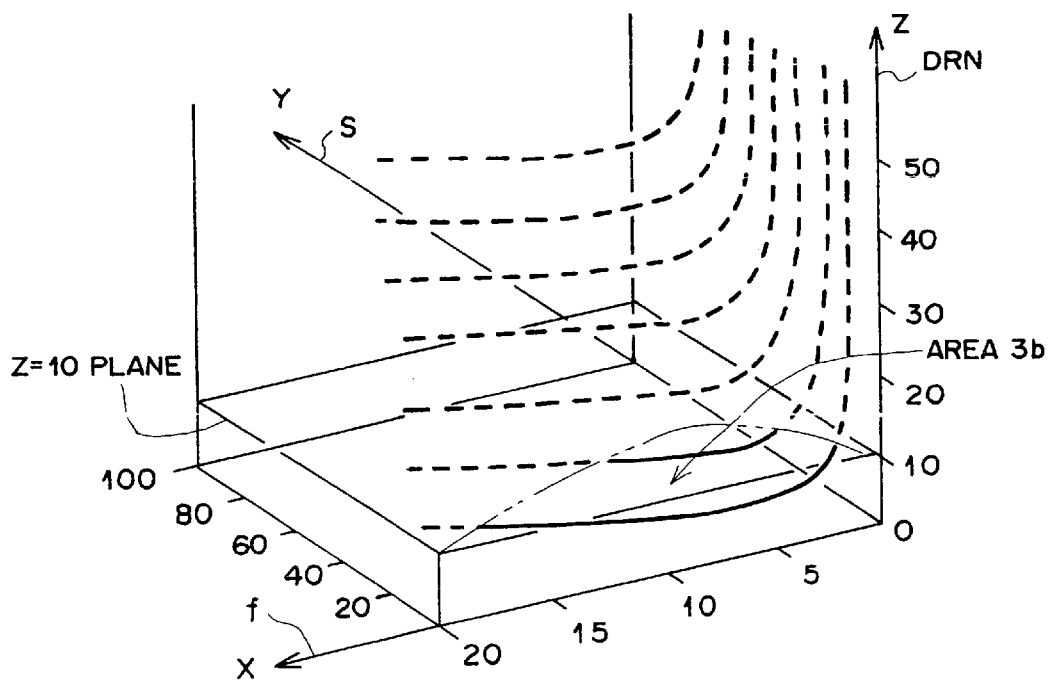
FIG. 7 is a graph showing relationship among the total number of noise charges DRN, the reading frequency f, and the area of one pixel S.
Figure 8:
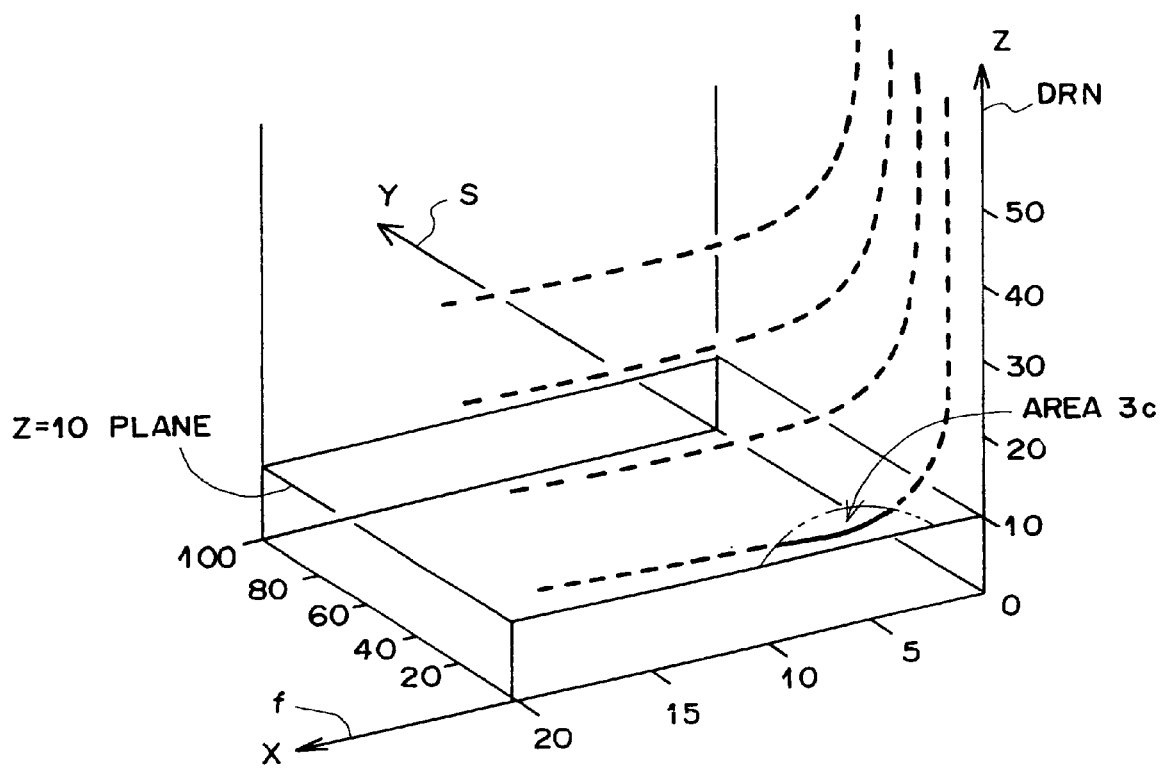
FIG. 8 is a graph showing relationship among the total number of noise charges DRN, the reading frequency f, and the area of one pixel S.

As a further different example, in cases where front exposure is performed by utilizing the CCD image sensor, it may be set such that T=0, 10, and 20 (° C.), N=250,000 (pieces), n=16 (pieces), M=1 (port), and texp=1/30 (sec). Also, the area of one pixel S may be varied by 10 ($\mu$m$^2$) stepwise from S=10 ($\mu$m$^2$) to S=100 ($\mu$m$^2$), and the reading frequency f may beset at various different values ranging from f=0.1 (megapixel/sec) to f=20 (megapixel/sec). In such cases, the relationship among the reading frequency f, the area of one pixel S, and the total number of noise charges DRN is represented by the three-dimensional graphs of FIG. 6, FIG. 7, and FIG. 8. In FIG. 6, FIG. 7, and FIG. 8, the reading frequency f is plotted on the X axis, the area of one pixel S is plotted on the Y axis, and the total number of noise charges DRN is plotted on the Z axis. As illustrated in FIG. 6, FIG. 7, and FIG. 8, the range of the setting, with which the total number of noise charges DRN occurring from one pixel (or the pixels processed as being equivalent to one pixel) can be restricted to be smaller than 10 (pieces), is the range indicated by the solid line lower than the Z=10 plane. The range is indicated as "Area 3a" in FIG. 6, "Area 3b" in FIG. 7, and "Area 3c" in FIG. 8. The graph of FIG. 6 is for the cases where T=0 (° C.). The graph of FIG. 7 is for the cases where T=10 (° C.). The graph of FIG. 8 is for the cases where T=20 (° C.).

As indicated by "Area 3a" in FIG. 6, in cases where T=0 (° C.), as the range of the setting, with which the total number of noise charges DRN occurring from one pixel (or the pixels processed as being equivalent to one pixel) can be restricted to be smaller than 10 (pieces), one of a wide variety of combinations of the values may be selected. However, as indicated by "Area 3b" in FIG. 7, in cases where the image sensor temperature T is T=10 (° C.), the range of the setting, with which the total number of noise charges DRN occurring from one pixel (or the pixels processed as being equivalent to one pixel) can be restricted to be smaller than 10 (pieces), becomes narrow. Also, as indicated by "Area 3c" in FIG. 8, in cases where the image sensor temperature T is T=20 (° C.), the range of the setting, with which the total number of noise charges DRN occurring from one pixel (or the pixels processed as being equivalent to one pixel) can be restricted to be smaller than 10 (pieces), becomes narrow even further.

As described above, the range of the setting satisfying the conditions of Formula (1), with which the total number of noise charges DRN occurring from one pixel (or the pixels processed as being equivalent to one pixel) can be restricted to be smaller than 10 (pieces), may be selected from various combinations of setting values.

In cases where the fluorescence endoscope system is constituted such that the intrinsic fluorescence image Zj is not guided through the image fiber and is directly formed on the image sensor, limitation represented by Formula (4) shown below is imposed upon the size of the image sensor.

$$\text{Focus} \times \tan\theta = D/2 \quad (4)$$

in which Focus represents the focal length of the image forming lens, $\theta$ represents a value ranging from 50 (deg) to 60 (deg), and D represents the length of the diagonal line of the image sensor. Specifically, in cases where the length of the diagonal line, D, of the image sensor is determined, limitation is imposed upon the relationship between the total number of pixels N and the area of one pixel S. Therefore, it is necessary for the range satisfying Formula (4) to be selected from the ranges described above, and the setting values of the image sensor are thereby determined.

In cases where back exposure is performed by utilizing the CCD image sensor, the quantum efficiency H becomes H=0.9 and thus becomes approximately two times as high as the quantum efficiency H in the front exposure. Therefore, in such cases, values may be set such that the total number of noise charges DRN becomes smaller than approximately 20.

In order for the intrinsic fluorescence Kj, which has been produced from a near point, to be detected as an image such that saturation may not be reached in the light receiving capacity of the imaging apparatus, the image sensor 25 is set in accordance with Formulas (2) and (3) in the manner described below.

A second image acquisition requirement of the fluorescence endoscope is that the intrinsic fluorescence Kj, which is produced from the normal tissues located at a position 5 mm spaced apart from the leading end of the measuring probe section 821 when the excitation light Le having a wavelength of 410 nm is irradiated to the normal tissues, be detected such that saturation may not be reached in the light receiving capacity of the pixel of the image sensor 25. Specifically, as illustrated in FIG. 2, it is required that, when the excitation light Le having an irradiation output of 100 mW is radiated out at a divergence angle of 120° from the radiating-out point Q of the irradiating lens 22, the intrinsic fluorescence Kj, which is produced from the normal tissues located at a position A 5 mm spaced apart from the radiating-out point Q, be acquired as an image such that saturation may not be reached in the light receiving capacity of the imaging apparatus.

As indicated by a point a1 in the bi-logarithmic graph of FIG. 3, the power density of the excitation light Le, which is irradiated to the position A with the setting described above, is equal to 0.4 (mW/mm$^2$), which is 100 times as high as the power density of the excitation light Le, which is irradiated to the position B. As in cases where the image of the cancerous tissues located at the position B is detected, the image of the intrinsic fluorescence Kj, which is produced from the normal tissues when the normal tissues are exposed to the excitation light Le having the power density of 0.4 (mW/mm$^2$), may be formed on the image sensor 25 by the image forming lens 23 and may be detected for an exposure time of 1/30 second. In such cases, for example, if the quantum efficiency H and the electron multiplication factor G of the image sensor 25 are equal to 1 and the area of one pixel S is 10 $\mu$m$^2$, the number of electric charges (the signal charges) accumulated at the pixel of the image sensor 25 will be equal to approximately 22,000, which is 1,000 times as large as the number of electric charges occurring in one pixel when the image of the cancerous tissues located at the position B is detected. (When the excitation light Le having an identical power density is irradiated to the normal tissues and the cancerous tissues, the normal tissues produce the intrinsic fluorescence Kj having an intensity approximately 10 times as high as the intensity of the intrinsic fluorescence Kj produced by the cancerous tissues. Also, in this case, the power density of the excitation light Le, which is irradiated to the position A, is 100 times as high as the power density of the excitation light Le, which is irradiated to the position B. Therefore, the number of electric charges accumulated at the pixel of the image sensor 25 is 1,000 times as large as the number of electric charges occurring in one pixel when the image of the cancerous tissues located at the position B is detected.)

Specifically, in order for the second image acquisition requirement to be satisfied when the electron multiplication factor G is equal to 1, it is necessary for the light receiving capacity of the imaging apparatus to be more than 1,000 times as high as the intensity of noise. Therefore, the dynamic range required of the imaging apparatus becomes wider than 1:1,000.

In cases where the fluorescence endoscope system is used in practice, it is necessary that the image of the cancerous tissues located at the remote point be acquired with a signal-to-noise ratio of at least 1, and a dynamic range capable of accommodating the intrinsic fluorescence Kj, which is produced from the normal tissues located at the near point, within the light receiving capacity of the imaging apparatus be obtained. Therefore, it is necessary for the image sensor 25 to be set such that the condition of Formula (1) is satisfied, and at the same time the conditions of Formulas (2) and (3) are satisfied. However, the number of electric charges Fd corresponding to the floating diffusion capacity is the value having relation to the reading frequency f, and the number of electric charges Fw corresponding to the full well capacity is the value having relation to the area of one pixel S. Therefore, the number of electric charges Fd corresponding to the floating diffusion capacity and the number of electric charges Fw corresponding to the full well capacity cannot be determined independently of the total number of noise charges DRN. Accordingly, as specific means for setting the image sensor 25 such that the condition of Formula (1) is satisfied, and at the same time the conditions of Formulas (2) and (3) are satisfied, the setting range for the image sensor 25 satisfying the first image acquisition requirement, i.e. Formula (1), may be determined by utilizing the graphs illustrated in FIGS. 4 to 8, and the like, and setting values for the image sensor 25 which satisfy the conditions of Formulas (2) and (3) i.e. the setting values capable of obtaining the dynamic range wider than 1:1,000, may then be selected from the setting range having been determined. In this manner, the setting values for the image sensor 25, which satisfy the first image acquisition requirement and the second image acquisition requirement., can be determined. Specifically, the setting values for the image sensor 25, which satisfy Formula (1), Formula (2), and Formula (3), can be determined.

Also, within the setting range for the image sensor 25 having been determined in the manner described above, the setting value of the image sensor temperature T may be fixed, and the value of the reading frequency f satisfying the condition RN=DN may be selected. In such cases, under the condition of the setting value of the image sensor temperature T, the first image acquisition requirement and the second image acquisition requirement are capable of being satisfied, and the total number of noise charges DRN is capable of being minimized.

Further, in cases where the image sensor 25 is constituted of the CCD type of image sensor or the MOS type of image sensor, the space for the image sensor is capable of being kept small. The CCD type of image sensor may be of the front exposure type or the back exposure type.

In the embodiment of the apparatus for acquiring a fluorescence image in accordance with the present invention, the image acquisition is performed by setting the imaging apparatus so as to satisfy Formulas (1), (2), and (3). Alternatively, the image acquisition may be performed by setting the imaging apparatus so as to satisfy only Formula (1). As another alternative, the image acquisition may be performed by setting the imaging apparatus so as to satisfy Formulas (2) and (3). In the former case, at least the effects of acquiring the image of the cancerous tissues, which are located at the remote point, with a signal-to-noise ratio of at least 1 are capable of being obtained. In the latter case, at least the effects of obtaining the dynamic range of at least 1:1,000 are capable of being obtained.

As described above, with the method and apparatus for acquiring a fluorescence image in accordance with the present invention, the image of the intrinsic fluorescence produced from a measuring site located at the remote point is capable of being acquired with a high signal-to-noise ratio, and the image of the intrinsic fluorescence produced from a measuring site located at the near point is capable of being acquired such that saturation is not reached in light receiving capacity of the imaging apparatus.

Embodiments of the fluorescence imaging apparatus in accordance with the present invention will be described hereinbelow.

Figure 9:
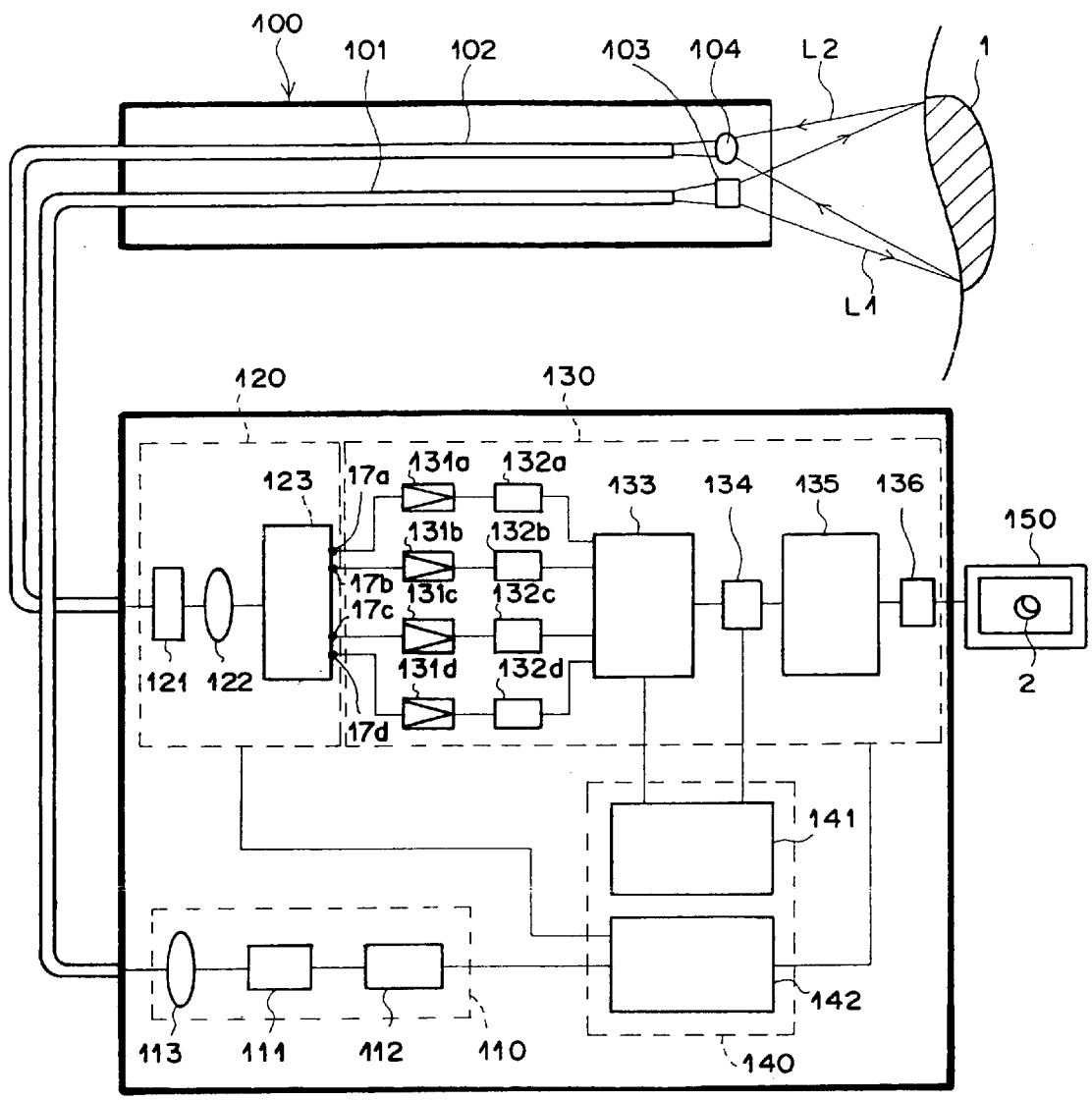
FIG. 9 is a schematic view showing an endoscope system, in which a first embodiment of the fluorescence imaging apparatus in accordance with the present invention is employed.

An endoscope system, in which a first embodiment of the fluorescence imaging apparatus in accordance with the present invention is employed, will be described hereinbelow with reference to FIG. 9 and FIG. 10. FIG. 9 is a schematic view showing the endoscope system, in which the first embodiment of the fluorescence imaging apparatus in accordance with the present invention is employed. In the endoscope system, excitation light is irradiated to a measuring site in a living body, and the fluorescence having been produced from the measuring site is guided through an image fiber and detected by a CCD image sensor having four output ports. Also, image signals having thus been detected are stored in an image memory and utilized for displaying a fluorescence image on a cathode ray tube (CRT) display device. When signal charges are read from the CCD image sensor, the signal charges are read at a reading frequency of 3.67 MHz, which is ¼ times as high as the conventional reading frequency of 14.7 MHz. Further, the endoscope system is provided with a look-up table for compensation for variations in output characteristics among the output ports of the CCD image sensor, and an image memory for storing the image signals having been obtained from the compensation.

The endoscope system, in which the first embodiment of the fluorescence imaging apparatus in accordance with the present invention is employed, comprises an endoscope 100 to be inserted into a region of a patient, which region is considered as being a diseased part, and an illuminating unit 110 provided with a light source for producing the excitation light, which is used for obtaining a fluorescence image. The endoscope system also comprises an imaging unit 120 for receiving the fluorescence, which has been produced from the measuring site in the living body when the excitation light is irradiated to the measuring site, and forming image signals representing the image of the fluorescence. The endoscope system further comprises an image processing unit 130 for performing image processing for displaying the fluorescence image, which has been detected by the imaging unit 120, as a visible image. The endoscope system still further comprises a control unit 140 for controlling the imaging operations. The endoscope system also comprises a CRT display device 150 for displaying the fluorescence image, which has been processed by the image processing unit 130, as a visible image.

A light guide 101 and an image fiber 102 extend in the endoscope 100 up to a leading end of the endoscope 100. An illuminating lens 103 is located at a leading end of the light guide 101, i.e. at the leading end of the endoscope 100. The image fiber 102 is constituted of glass fibers, and a converging lens 104 is located at a leading end of the image fiber 102. The light guide 101 is constituted of a quartz glass fiber and is connected to the illuminating unit 110.

The illuminating unit 110 comprises a GaN type of semiconductor laser 111 for producing excitation light L1, which is used for obtaining a fluorescence image, and an electric power source 112, which is electrically connected to the GaN type of semiconductor laser 111.

The imaging unit 120 comprises an excitation light cut-off filter 121 for filtering out light, which has wavelengths falling within a wavelength region of at most 430 nm in the vicinity of the wavelength of the excitation light L1, from fluorescence L2 having passed through the image fiber 102. The imaging unit 120 also comprises a CCD image sensor 123.

As illustrated in FIG. 10, the CCD image sensor 123 is provided with an imaging surface 11, which comprises an array of n×m pixels. A region inward from a circle inscribed in the peripheral sides of the imaging surface 11 is an image exposure region 12, which is utilized for the imaging. Regions outward from the image exposure region 12 in the imaging surface 11 are non-exposure regions 13, 13, which are blocked by thin metal films, and the like. The imaging surface 11 is divided into four imaging blocks 14a, 14b, 14c, and 14d. Horizontal shift registers 15a, 15b, 15c, and 15d are provided respectively for the imaging blocks 14a, 14b, 14c, and 14d. The horizontal shift registers 15a, 15b, 15c, and 15d are connected respectively to output circuits 16a, 16b, 16c, and 16d. The output circuits 16a, 16b, 16c, and 16d are connected respectively to output ports 17a, 17b, 17c, and 17d.

The image processing unit 130 comprises amplifiers 131a, 131b, 131c, and 131d for amplifying image signals, which have been obtained from the CCD image sensor 123. The image processing unit 130 also comprises analog-to-digital converting circuits 132a, 132b, 132c, and 132d for digitizing the image signals, which have been amplified respectively by the amplifiers 131a, 131b, 131c, and 131d. The image processing unit 130 further comprises an image memory 133 for storing the image signals having been digitized, and a look-up table 134 for performing transform of the image signal having been received from the image memory 133. The image processing unit 130 still further comprises an image memory 135 for storing the image signal having been obtained from the look-up table 134, and a digital-to-analog converter 136 for performing digital-to-analog conversion of the image signal and feeding the obtained analog image signal into the CRT display device 150.

The control unit 140 comprises a correction control section 141 for controlling the correcting operations for compensation for variations in image signal output characteristics. The control unit 140 also comprises a timing control section 142, which is connected to the respective units and controls the operation timings. The correction control section 141 is connected to the image memory 133 and the look-up table 134.

The CCD image sensor 123 constitutes the imaging means of the fluorescence imaging apparatus in accordance with the present invention. The look-up table 134 constitutes the signal transforming means of the fluorescence imaging apparatus in accordance with the present invention. The image memory 133 constitutes the composing means of the fluorescence imaging apparatus in accordance with the present invention. The correction control section 141 constitutes the correction value calculating means and the correction value setting means of the fluorescence imaging apparatus in accordance with the present invention.

How the endoscope system, in which the first embodiment of the fluorescence imaging apparatus in accordance with the present invention is employed, operates will be described hereinbelow.

The electric power source 112 for the GaN type of semiconductor laser 111 is driven in accordance with a control signal fed from the timing control section 142, and the excitation light L1 having a wavelength of 410 nm is produced by the GaN type of semiconductor laser 111. The excitation light L1 passes through a lens 113 and impinges upon the light guide 101. The excitation light L1 is guided through the light guide 101 to the leading end of the endoscope 100 and is irradiated through the illuminating lens 103 to a measuring site 1.

When the measuring site 1 is exposed to the excitation light L1, the fluorescence L2 is produced from the measuring site 1. The fluorescence L2 is converged by the converging lens 104 and impinges upon the leading end of the image fiber 102. The fluorescence L2 then passes through the image fiber 102 and impinges upon the excitation light cut-off filter 121 of the imaging unit 120. Light, which has wavelengths falling within a wavelength region of at most 430 nm in the vicinity of the wavelength of the excitation light L1, is filtered out from the fluorescence L2 by the excitation light cut-off filter 121, and an image of the fluorescence L2 is formed on the CCD image sensor 123 by a lens 122.

In the CCD image sensor 123, the fluorescence L2 is photoelectrically converted by the imaging surface 11, and the resulting signal charges are accumulated at pixels of the imaging blocks 14a, 14b, 14c, and 14d. The signal charges, which have been accumulated in the imaging blocks 14a, 14b, 14c, and 14d, are transferred respectively with predetermined timings into the horizontal shift registers 15a, 15b, 15c, and 15d and converted by the output circuits 16a, 16b, 16c, and 16d from voltage signals to electric current image signals. The thus obtained image signals are fed out from the output ports 17a, 17b, 17c, and 17d.

Also, in accordance with a control signal fed from the timing control section 142, the image signals, which have been detected respectively by the imaging blocks 14a, 14b, 14c, and 14d, are read with a reading frequency of 3.67 MHz from the output ports 17a, 17b, 17c, and 17d and fed into the amplifiers 131a, 131b, 131c, and 131d of the image processing unit 130.

The image signals, which have been amplified by the amplifiers 131a, 131b, 131c, and 131d, are digitized respectively (by the analog-to-digital converting circuits 132a, 132b, 132c, and 132d. The thus obtained digital image signals are stored in the image memory 133.

The correction control section 141 reads the image signals from the image memory 133 and calculates correction values for compensation for variations in output characteristics among the four output channels, which extend from the imaging blocks 14a, 14b, 14c, and 14d of the CCD image sensor 123 to the image memory 133. The correction values are calculated in the manner described below.

Firstly, the correction control section 141 calculates the mean value of the signal intensities of the image signal, which has been detected in the non-exposure region of each of the imaging blocks 14a, 14b, 14c, and 14d. Also, for each of the imaging blocks 14b, 14c, and 14d, an offset value is calculated such that the mean value obtained for each imaging block may become approximately identical with the mean value calculated for the imaging block 14a.

Thereafter, the offset value for the imaging block 14b is subtracted from the signal intensities of the image signal, which has been detected in the image exposure region of the imaging block 14b. In the same manner, the offset values for the imaging blocks 14c and 14d are subtracted respectively from the signal intensities of the image signals, which have been detected in the image exposure regions of the imaging blocks 14c and 14d. Thereafter, the signal intensity of the image signal, which has been detected at the right end of the imaging block 14a, and the signal intensity of the image signal, which has been detected at the left end of the imaging block 14b, are compared with each other. A tone curve correction value for the imaging block 14b is then calculated such that the signal intensity of the image signal, which has been detected at the left end of the imaging block 14b, may become approximately identical with the signal intensity of the image signal, which has been detected at the right end of the imaging block 14a. By the utilization of the tone curve correction value for the imaging block 14b, the signal intensities for the imaging block 14b are calculated again. Also, the signal intensity of the image signal, which has been detected at the right end of the imaging block 14c, and the signal intensity of the image signal, which has been detected at the left end of the imaging block 14d, are compared with each other. A temporary tone curve correction value for the imaging block 14d is then calculated such that the signal intensity of the image signal, which has been detected at the left end of the imaging block 14d, may become approximately identical with the signal intensity of the image signal, which has been detected at the right end of the imaging block 14c. By the utilization of the tone curve correction value for the imaging block 14d, the signal intensities for the imaging block 14d are calculated again. Further, the signal intensities of the image signals, which correspond to the lower end of the imaging block 14a and the lower end of the imaging block 14b, and the signal intensities of the image signals, which correspond to the upper end of the imaging block 14c and the upper end of the imaging block 14d, are compared with each other. Tone curve correction values for the imaging blocks 14c and 14d are then calculated such that the signal intensities of the image signals, which correspond to the upper end of the imaging block 14c and the upper end of the imaging block 14d, may become approximately identical with the signal intensities of the image signals, which correspond to the lower end of the imaging block 14a and the lower end of the imaging block 14b.

The correction control section 141 sets the offset values and the tone curve correction values, which correspond to the imaging blocks 14b, 14c, and 14d, in the look-up table 134. Also, the image signals, which have been detected respectively in the imaging blocks 14a, 14b, 14c, and 14d, are read from the image memory 133 and fed into the look-up table 134. In the look-up table 134, the image signals are transformed by use of the offset values and the tone curve correction values, which correspond to the respective imaging blocks. The image signal having been obtained from the look-up table 134 is stored in the image memory 135. The image signal, which has been detected in the imaging block 14a, is transformed in one-to-one relationship in the look-up table 134 and stored in the image memory 135.

The image signal having been fed out from the image memory 135 is subjected to the digital-to-analog conversion in the digital-to-analog converter 136. The image signal obtained from the digital-to-analog converter 136 is utilized for displaying a fluorescence image 2 on the CRT display device 150.

As described above, the CCD image sensor 123 has the four output ports, and the number of pixels allocated to one output port reduces to ¼. Therefore, even if the reading frequency is reduced to a value ¼ times as high as the ordinary reading frequency, the signal charges of all pixels are capable of being read within the reading time. Accordingly, reading noise is capable of being suppressed and the signal-to-noise ratio of the detected image is capable of being enhanced, such that adverse effects do not occur on displaying of the fluorescence image as a dynamic image.

Also, the correction values are calculated in accordance with variations in output characteristics among the four output channels, which extend from the four imaging blocks 14a, 14b, 14c, and 14d to the image memory 133. The calculated correction values are set in the look-up table 134. Therefore, the variations in output characteristics among the four output channels are capable of being compensated for, and the problems are capable of being prevented from occurring in that division line patterns appear in the formed image.

In cases where the look-up table 134, which stores the offset values and the tone curve correction values, is utilized, the compensation for the output characteristics is capable of being performed easily.

Further, each of the imaging blocks 14a, 14b, 14c, and 14d contains one of the non-exposure regions. Therefore, the offset values and the tone curve correction values, which act as the correction values, are capable of being calculated from the image signals having been detected with the ordinary imaging operation of the CCD image sensor 123, and the calculated values are capable of being set in the look-up table 134. Accordingly, the collecting operations are capable of being performed such that the ordinary imaging operation is not obstructed.

Are endoscope system, in which a second embodiment of the fluorescence imaging apparatus in accordance with the present invention is employed, will be described hereinbelow with reference to FIG. 11. FIG. 11 is a schematic view showing the endoscope system, in which the second embodiment of the fluorescence imaging apparatus in accordance with the present invention is employed. In the endoscope system, excitation light is irradiated to the measuring site in a living body, and the fluorescence having been produced from the measuring site is guided through the image fiber and detected by the CCD image sensor having four output ports. Also, the image signals having thus been detected are stored in the image memory and utilized for displaying a fluorescence image on the CRT display device. When signal charges are read from the CCD image sensor, the signal charges are read at a reading frequency of 3.67 MHz, which is ¼ times as high as the conventional reading frequency. Further, the endoscope system is provided with look-up tables for compensation for variations in output characteristics among the output ports of the CCD image sensor. The look-up tables are located at the stage preceding to the image memory.

In FIG. 11, similar elements are numbered with the same reference numerals with respect to FIG. 9.

The endoscope system, in which the second embodiment of the fluorescence imaging apparatus in accordance with the present invention is employed, comprises the endoscope 100 to be inserted into a region of a patient, which region is considered as being a diseased part, and the illuminating unit 110 provided with the light source for producing the excitation light, which is used for obtaining a fluorescence image. The endoscope system also comprises the imaging unit 120 for receiving the fluorescence, which has been produced from the measuring site in the living body when the excitation light is irradiated to the measuring site, and forming image signals representing the image of the fluorescence. The endoscope system further comprises an image processing unit 200 for performing image processing for displaying the fluorescence image, which has been detected by the imaging unit 120, as a visible image. The endoscope system still further comprises a control unit 210 for controlling the imaging operations. The endoscope system also comprises the CRT display device 150 utilized for displaying the fluorescence image, which has been processed by the image processing unit 200, as a visible image.

The image processing unit 200 comprises the amplifiers 131*a*, 131*b*, 131*c*, and 131*d* for amplifying the image signals, which have been obtained from the CCD image sensor 123. The image processing unit 200 also comprises the analog-to-digital converting circuits 132*a*, 132*b*, 132*c*, and 132*d* for digitizing the image signals, which have been amplified respectively by the amplifiers 131*a*, 131*b*, 131*c*, and 131*d*. The image processing unit 200 further comprises look-up tables 201*a*, 201*b*, 201*c*, and 201*d* for performing transform of the digitized image signals, and compensating for output characteristics. The image processing unit 200 still further comprises an image memory 202 for storing the image signals having been obtained from the compensation for the output characteristics. The image processing unit 200 also comprises the digital-to-analog converter 136 for performing digital-to-analog conversion of the image signal, which has been received from the image memory 202, and feeding the obtained analog image signal into the CRT display device 150. The look-up table 201*a* is a look-up table for performing the signal transform in one-to-one relationship. The look-up tables 201*b*, 201*c*, and 201*d* are look-up tables, in which offset values and tone curve correction values are capable of being set.

The control unit 210 comprises a correction control section 211 for controlling the correcting operations for compensation for variations in image signal output characteristics. The control unit 210 also comprises a timing control section 212, which is connected to the respective units and controls the operation timings. The correction control section 211 is connected to the image memory 202 and the look-up tables 201*b*, 201*c*, and 201*d*.

The CCD image sensor 123 constitutes the imaging means of the fluorescence imaging apparatus in accordance with the present invention. The look-up tables 201*a*, 201*b*, 201*c*, and 201*d* constitute the signal transforming means of the fluorescence imaging apparatus in accordance with the present invention. The image memory 202 constitutes the composing means of the fluorescence imaging apparatus in accordance with the present invention. The correction control section 211 constitutes the re-setting judgment means, the correction value calculating means, and the correction value setting means of the fluorescence imaging apparatus in accordance with the present invention.

How the endoscope system, in which the second embodiment of the fluorescence imaging apparatus in accordance with the present invention is employed, operates will be described hereinbelow.

In accordance with a control signal fed from the timing control section 212, the excitation light L1 having a wavelength of 410 nm is produced by the GaN type of semiconductor laser 111 and irradiated to the measuring site 1.

The fluorescence L2, which has been produced from the measuring site 1, passes through the image fiber 102 and impinges upon the excitation light cut-off filter 121 of the imaging unit 120. The image of the fluorescence L2 is formed on the CCD image sensor 123.

In accordance with a control signal fed from the timing control section 212, the image signals, which have been detected respectively by the imaging blocks 14*a*, 14*b*, 14*c*, and 14*d*, are read with a reading frequency of 3.67 MHz from the output ports 17*a*, 17*b*, 17*c*, and 17*d* of the CCD image sensor 123 and fed into the amplifiers 131*a*, 131*b*, 131*c*, and 131*d* of the image processing unit 200.

The image signals, which have been amplified by the amplifiers 131*a*, 131*b*, 131*c*, and 131*d*, are digitized respectively by the analog-to-digital converting circuits 132*a*, 132*b*, 132*c*, and 132*d*. The thus obtained digital image signals are subjected to the signal transform in the look-up tables 201*a*, 201*b*, 201*c*, and 201*d*. The image signals having been obtained from the signal transform are stored in the image memory 202. In accordance with correcting operations having been performed previously, the offset values and the tone curve correction values, which act as the correction values for compensations for variations in output characteristics, are stored in the look-up tables 201*b*, 201*c*, and 201*d*.

The correction control section 211 read the image signal, which has been detected in the non-exposure region of the imaging block 14*a* of the CCD image sensor 123, from the image memory 202. The correction control section 211 calculates the mean value of the signal intensities of the thus read image signal. Also, the correction control section 211 makes a judgment as to whether the calculated mean value has or has not changed by at least a predetermined value from a reference mean value. The signal intensities of the image signal, which has been detected in the non-exposure region of the imaging block 14*a*, reflect the ambient temperature. Also, it has been known that, if the ambient temperature does not change, little alteration occurs in the variations in output characteristics among the output channels. Therefore, in cases where a change by at least the predetermined value does not occur in the aforesaid mean value, it may be regarded that no change has occurred in the output characteristics among the four output channels.

Therefore, in cases where it has been judged that a change by at least the predetermined value has not occurred in the mean value of the signal intensities of the image signal having been detected in the non-exposure region, the correction control section 211 does not perform the re-calculations and the re-setting of the offset values and the tone curve correction values.

In such cases, in accordance with the control performed by the timing control section 212, the ordinary image processing operation is performed. Also, the image signal having been fed out from the image memory 202 is subjected to the digital-to-analog conversion in the digital-to-analog converter 136. The image signal obtained from the digital-to-analog converter 136 is utilized for displaying the fluorescence image 2 on the CRT display device 150.

In cases where it has been judged that a change by at least the predetermined value has occurred in the mean value of the signal intensities of the image signal having been detected in the non-exposure region, as in the correction control section 141 in the first embodiment of FIG. 9, the image signal having been detected by the imaging block 14*a* of the imaging surface 11 is taken as a reference image signal, and the offset values and the tone curve correction values for the compensation for variations in output characteristics among the output channels are calculated again. Also, the new offset values and the new tone curve correction values having thus been calculated are set in the look-up tables 201*b*, 201*c*, and 201*d*. With the imaging operation performed after the correction values have thus been set again, an image having been corrected with the new correction values is displayed.

The look-up table 201a is a look-up table for performing the signal transform in one-to-one relationship. In the second embodiment, the look-up table 201a is provided in order to minimize the variations in output characteristics. However, the look-up table 201a may be omitted.

With the second embodiment of the fluorescence imaging apparatus in accordance with the present invention, the same effects as those with the first embodiment of the fluorescence imaging apparatus in accordance with the present invention can be obtained. Also, with the second embodiment, the number of times of calculations of new correction values is capable of being reduced, and the processing time required to make the compensation for the output characteristics is capable of being kept short. Further, a particular image memory for storing the image signals having been obtained from the compensation for the output characteristics need not be provided. Therefore, the constitution of the signal processing circuit is capable of being simplified.

An endoscope system, in which a third embodiment of the fluorescence imaging apparatus in accordance with the present invention is employed, will be described hereinbelow with reference to FIG. 12. FIG. 12 is a schematic view showing the endoscope system, in which the third embodiment of the fluorescence imaging apparatus in accordance with the present invention is employed. In the endoscope system, excitation light is irradiated to the measuring site in a living body, and the fluorescence having been produced from the measuring site is guided through the image fiber and detected by the CCD image sensor having four output ports. In this manner, the fluorescence image is displayed on the CRT display device. When signal charges are read from the CCD image sensor, the signal charges are read at a reading frequency of 3.67 MHz, which is ¼ times as high as the conventional reading frequency. Further, each of the output ports of the CCD image sensor is provided with one of amplifiers, in which the offset values and gains are capable of being adjusted. The amplifiers perform amplification of the image signals and the compensation for the output characteristics. In FIG. 12, similar elements are numbered with the same reference numerals with respect to FIG. 11.

The endoscope system, in which the third embodiment of the fluorescence imaging apparatus in accordance with the present invention is employed, comprises the endoscope 100 to be inserted into a region of a patient, which region is considered as being a diseased part, and the illuminating unit 110 provided with the light source for producing the excitation light, which is used for obtaining a fluorescence image. The endoscope system also comprises the imaging unit 120 for receiving the fluorescence, which has been produced from the measuring site in the living body when the excitation light is irradiated to the measuring site, and forming image signals representing the image of the fluorescence. The endoscope system further comprises an image processing unit 300 for performing image processing for displaying the fluorescence image, which has been detected by the imaging unit 120, as a visible image. The endoscope system still further comprises a control unit 310 for controlling the imaging operations. The endoscope system also comprises the CRT display device 150 for displaying the fluorescence image, which has been processed by the image processing unit 300, as a visible image.

The image processing unit 300 comprises amplifiers 301a, 301b, 301c, and 301d for amplifying the image signals, which have been obtained from the CCD image sensor 123. The image processing unit 300 also comprises the analog-to-digital converting circuits 132a, 132b, 132c, and 132d for digitizing the image signals, which have been amplified respectively by the amplifiers 301a, 301b, 301c, and 301d. The image processing unit 300 further comprises an image memory 302 for storing the digitized image signals. The image processing unit 300 still further comprises the digital-to-analog converter 136 for performing digital-to-analog conversion of the image signal, which has been received from the image memory 302, and feeding the obtained analog image signal into the CRT display device 150.

The control unit 310 comprises a correction control section 311 for controlling the correcting operations for compensation for variations in image signal output characteristics. The control unit 310 also comprises a timing control section 312, which is connected to the respective units and controls the operation timings. The correction control section 311 is connected to the image memory 302 and the amplifiers 301b, 301c, and 301d.

The amplifiers 301a, 301b, 301c, and 301d constitute the amplification means of the fluorescence imaging apparatus in accordance with the present invention. The image memory 302 constitutes the composing means of the fluorescence imaging apparatus in accordance with the present invention. The correction control section 311 constitutes the re-setting judgment means, the correction value calculating means, and the correction value setting means of the fluorescence imaging apparatus in accordance with the present invention.

How the endoscope system, in which the third embodiment of the fluorescence imaging apparatus in accordance with the present invention is employed, operates will be described hereinbelow.

In accordance with a control signal fed from the timing control section 312, the excitation light L1 having a wavelength of 410 nm is produced by the GaN type of semiconductor laser 111 and irradiated to the measuring site 1.

The fluorescence L2, which has been produced from the measuring site 1, passes through the image fiber 102 and impinges upon the excitation light cut-off filter 121 of the imaging unit 120. The image of the fluorescence L2 is formed on the CCD image sensor 123.

In accordance with a control signal fed from the timing control section 312, the image signals, which have been detected respectively by the imaging blocks 14a, 14b, 14c, and 14d, are read with a reading frequency of 3.67 MHz from the output ports 17a, 17b, 17c, and 17d of the CCD image sensor 123 and fed into the amplifiers 301a, 301b, 301c, and 301d of the image processing unit 300.

The image signals, which have been amplified by the amplifiers 301a, 301b, 301c, and 301d, are digitized respectively by the analog-to-digital converting circuits 132a, 132b, 132c, and 132d. The thus obtained digital image signals are stored in the image memory 302. In accordance with correcting operations having been performed previously, the offset values and the gains of the amplifiers 301b, 301c, and 301d have been adjusted at the values for compensation for variations in output characteristics.

As in the correction control section 211 illustrated in FIG. 11, the correction control section 311 read the image signal, which has been detected in the non-exposure region of the imaging block 14a of the CCD image sensor 123, from the image memory 302. The correction control section 311 calculates the mean value of the signal intensities of the thus read image signal. Also, the correction control section 311 makes a judgment as to whether the calculated mean value has or has not changed by at least a predetermined value from a reference mean value. In cases where it has been judged that a change by at least the predetermined value has not occurred in the mean value of the signal intensities of the image signal having been detected in the non-exposure region, the correction control section 311 does not perform the re-calculations and the re-setting of the offset values and the gain adjustment values, which act as the correction values. In such cases, the ordinary image processing operation is performed. Also, the image signal having been fed out from the image memory 302 is subjected to the digital-to-analog conversion in the digital-to-analog converter 136. The image signal obtained from the digital-to-analog converter 136 is utilized for displaying the fluorescence image 2 on the CRT display device 150.

In cases where it has been judged that a change by at least the predetermined value has occurred in the mean value of the signal intensities of the image signal having been detected in the non-exposure region, the correction control section 311 calculates the offset values and the gain adjustment values, which act as the correction values, in the manner described below.

Firstly, the correction control section 311 calculates the mean value of the signal intensities of the image signal, which has been detected in the non-exposure region of each of the imaging blocks 14a, 14b, 14c, and 14d. Also, for each of the imaging blocks 14b, 14c, and 14d, an offset value is calculated such that the mean value obtained for each imaging block may become approximately identical with the mean value calculated for the imaging block 14a.

Thereafter, the offset value for the imaging block 14b is subtracted from the signal intensities of the image signal, which has been detected in the image exposure region of the imaging block 14b. In the same manner, the offset values for the imaging blocks 14c and 14d are subtracted respectively from the signal intensities of the image signals, which have been detected in the image exposure regions of the imaging blocks 14c and 14d. Thereafter, the signal intensity of the image signal, which has been detected at the right end of the imaging block 14a, and the signal intensity of the image signal, which has been detected at the left end of the imaging block 14b, are compared with each other. A gain adjustment value for the imaging block 14b is then calculated such that the signal intensity of the image signal, which has been detected at the left end of the imaging block 14b, may become approximately identical with the signal intensity of the image signal, which has been detected at the right end of the imaging block 14a. By the utilization of the gain adjustment value for the imaging block 14b, the signal intensities for the imaging block 14b are calculated again. Also, the signal intensity of the image signal, which has been detected at the right end of the imaging block 14c, and the signal intensity of the image signal, which has been detected at the left end of the imaging block 14d, are compared with each other. A temporary gain adjustment value for the imaging block 14d is then calculated such that the signal intensity of the image signal, which has been detected at the left end of the imaging block 14d, may become approximately identical with the signal intensity of the image signal, which has been detected at the right end of the imaging block 14c. By the utilization of the gain adjustment value for the imaging block 14d, the signal intensities for the imaging block 14d are calculated again. Further, the signal intensities of the image signals, which correspond to the lower end of the imaging block 14a and the lower end of the imaging block 14b, and the signal intensities of the image signals, which correspond to the upper end of the imaging block 14c and the upper end of the imaging block 14d, are compared with each other. Gain adjustment values for the imaging blocks 14c and 14d are then calculated such that the signal intensities of the image signals, which correspond to the upper end of the imaging block 14c and the upper end of the imaging block 14d, may become approximately identical with the signal intensities of the image signals, which correspond to the lower end of the imaging block 14a and the lower end of the imaging block 14b.

The correction control section 311 adjusts the offset values and the gains of the amplifiers 301b, 301c, and 301d by utilizing the offset values and the gain adjustment values, which correspond to the imaging blocks 14b, 14c, and 14d.

With the imaging operation performed after the correction values have thus been set again, the image signals having been corrected with the new correction values are stored in the image memory 302 and utilized for displaying a fluorescence image on the CRT display device 150.

With the third embodiment of the fluorescence imaging apparatus in accordance with the present invention, the same effects as those with the second embodiment of the fluorescence imaging apparatus in accordance with the present invention can be obtained. Also, with the third embodiment, amplifiers, which have heretofore been provided in a signal processing circuit, can be utilized as the correction means for compensating for variations in output characteristics. Therefore, new circuit parts need not be provided, the signal processing circuit is capable of being kept simple, and the production cost is capable of being kept low.

Figure 13:
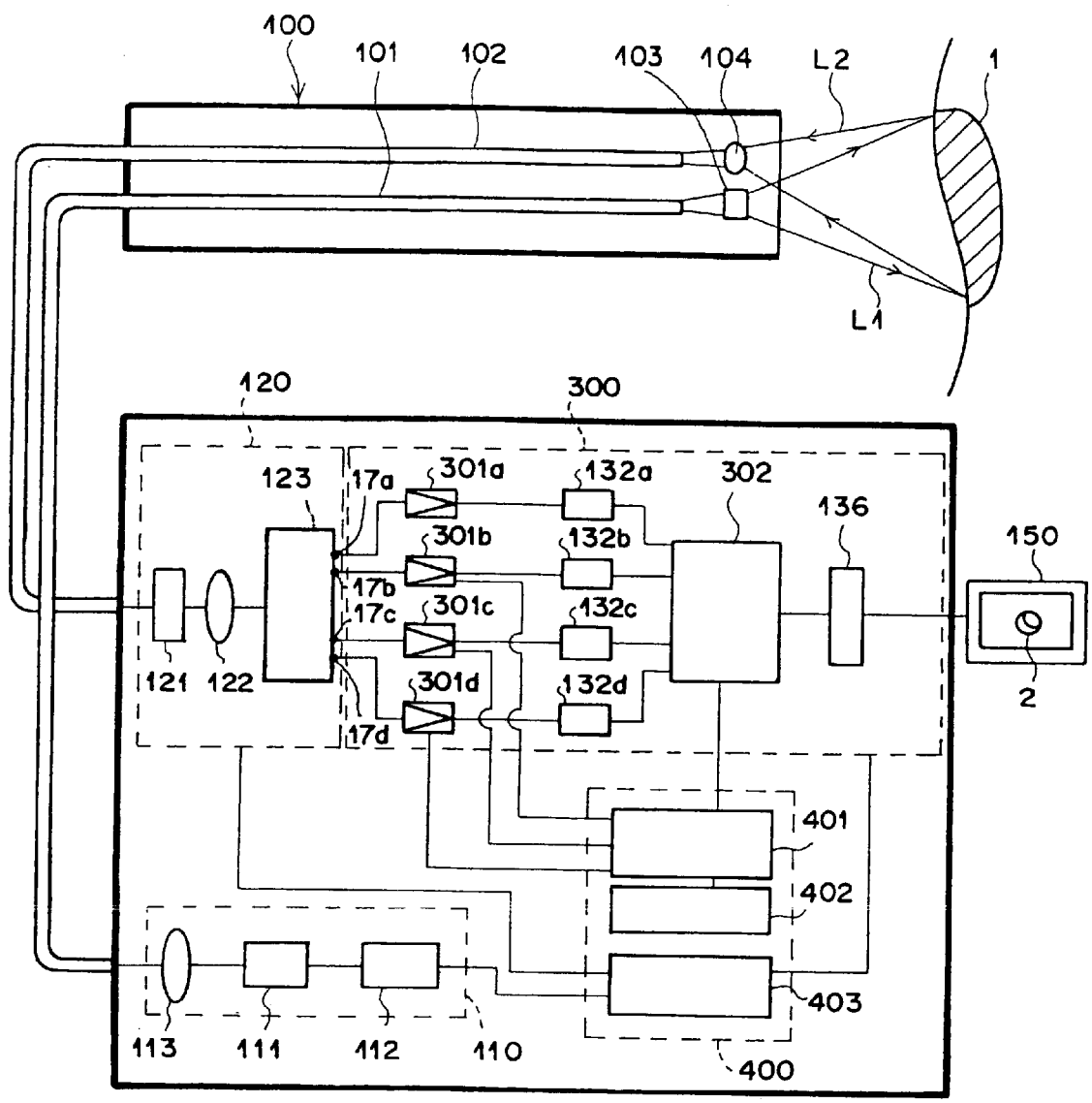
FIG. 13 is a schematic view showing an endoscope system, in which a fourth embodiment of the fluorescence imaging apparatus in accordance with the present invention is employed.

An endoscope system, in which a fourth embodiment of the fluorescence imaging apparatus in accordance with the present invention is employed, will be described hereinbelow with reference to FIG. 13. FIG. 13 is a schematic view showing the endoscope system, in which the fourth embodiment of the fluorescence imaging apparatus in accordance with the present invention is employed. In the endoscope system, excitation light is irradiated to the measuring site in a living body, and the fluorescence having been produced from the measuring site is guided through the image fiber and detected by the CCD image sensor having four output ports. In this manner, the fluorescence image is displayed on the CRT display device. When signal charges are read from the CCD image sensor, the signal charges are read at a reading frequency of 3.67 MHz, which is ¼ times as high as the conventional reading frequency. Further, each of the output ports of the CCD image sensor is provided with one of amplifiers, in which the offset values and gains are capable of being adjusted. The amplifiers perform amplification of the image signals and the compensation for the output characteristics. Also, the endoscope system is provided with a correction value storing section for storing mean values of signal intensities of image signals having been detected in the state, in which light is blocked from impinging upon the imaging surface of the CCD image sensor, and the corresponding offset values and the corresponding gain adjustment values, which are to be set as the correction values in the amplifiers. In FIG. 13, similar elements are numbered with the same reference numerals with respect to FIG. 12.

The endoscope system, in which the fourth embodiment of the fluorescence imaging apparatus in accordance with the present invention is employed, comprises the endoscope 100 to be inserted into a region of a patient, which region is considered as being a diseased part, and the illuminating unit 110 provided with the light source for producing the excitation light, which is used for obtaining a fluorescence image. The endoscope system also comprises the imaging unit 120 for receiving the fluorescence, which has been produced from the measuring site in the living body when the excitation light is irradiated to the measuring site, and forming image signals representing the image of the fluorescence. The endoscope system further comprises the image processing unit 300 for performing image processing for displaying the fluorescence image, which has been detected by the imaging unit 120, as a visible image. The endoscope system still further comprises a control unit 400 for controlling the imaging operations. The endoscope system also comprises the CRT display device 150 utilized for displaying the fluorescence image, which has been processed by the image processing unit 300, as a visible image.

The control unit 400 comprises a correction control section 401 for controlling the correcting operations for compensation for variations in image signal output characteristics. The control unit 400 also comprises a correction value storing section 402 for storing previously the mean values of signal intensities of image signals having been detected by the imaging block 14a in the state, in which light is blocked from impinging upon the imaging surface 11 of the CCD image sensor 123, and the corresponding offset values and the corresponding gain adjustment values, which act as the correction values. The control unit 400 further comprises a timing control section 403, which is connected to the respective units and controls the operation timings. The correction control section 401 is connected to the image memory 302 and the amplifiers 301b, 301c, and 301d.

The correction control section 401 read the image signal having been detected by the imaging block 14a in the state, in which light is blocked from impinging upon the imaging surface 11 of the CCD image sensor 123, from the image memory 302. The correction control section 401 calculates the mean value of the signal intensities of the thus read image signal. Also, the correction control section 401 makes a judgment as to whether the calculated mean value has or has not changed by at least a predetermined value from a reference mean value. In cases where it has been judged that a change by at least the predetermined value has not occurred in the mean value of the signal intensities of the image signal described above, the correction control section 401 does not perform the re-setting of the offset values and the gain adjustment values, which act as the correction values. In such cases, the ordinary image processing operation is performed.

In cases where it has been judged that a change by at least the predetermined value has occurred in the mean value of the signal intensities of the image signal described above, the correction control section 401 selects the offset values and the gain adjustment values, which correspond to the mean value, from among the offset values and the gain adjustment values having been stored in the correction value storing section 402. The offset values and the gain adjustment values having thus been selected are set as the correction values.

The amplifiers 301a, 301b, 301c, and 301d constitute the amplification means of the fluorescence imaging apparatus in accordance with the present invention. The image memory 302 constitutes the composing means of the fluorescence imaging apparatus in accordance with the present invention. The correction control section 401 constitutes the re-setting judgment means and the correction value setting means of the fluorescence imaging apparatus in accordance with the present invention. The correction value storing section 402 constitutes the correction value storing means of the fluorescence imaging apparatus in accordance with the present invention.

How the endoscope system, in which the fourth embodiment of the fluorescence imaging apparatus in accordance with the present invention is employed, operates will be described hereinbelow.

The correction value storing section 402 stores previously the mean values of signal intensities of image signals having been detected by the imaging block 14a in the state, in which light is blocked from impinging upon the imaging surface 11 of the CCD image sensor 123, and the offset values and the gain adjustment values, which act as the correction values corresponding to the respective mean values. The image signals, from which the mean values are calculated, are the ones having been obtained with respect to various different temperatures falling within the temperature range, at which the endoscope system is used. Also, the offset values and the gain adjustment values have been calculated in the same manner as that in the calculations of the offset values and the gain adjustment values in the third embodiment of FIG. 12.

When an imaging operation is to be performed, firstly, in accordance with a control signal fed from the timing control section 403, image signals are detected in the state, in which light is blocked from impinging upon the imaging surface 11. The thus detected image signals are fed into the amplifiers 301a, 301b, 301c, and 301d of the image processing unit 300. Thereafter, the excitation light L1 having a wavelength of 410 nm is produced by the GaN type of semiconductor laser 111 and irradiated to the measuring site 1.

The fluorescence L2, which has been produced from the measuring site 1, passes through the image fiber 102 and impinges upon the excitation light cut-off filter 121 of the imaging unit 120. The image of the fluorescence L2 is formed on the CCD image sensor 123.

In accordance with a control signal fed from the timing control section 403, the image signals, which have been detected respectively by the imaging blocks 14a, 14b, 14c, and 14d, are read with a reading frequency of 3.67 MHz from the output ports 17a, 17b, 17c, and 17d of the CCD image sensor 123 and fed into the amplifiers 301a, 301b, 301c, and 301d of the image processing unit 300.

In the amplifiers 301a, 301b, 301c, and 301d, the image signals are amplified successively. The image signals, which have been amplified by the amplifiers 301a, 301b, 301c, and 301d, are digitized respectively by the analog-to-digital converting circuits 132a, 132b, 132c, and 132d. The thus obtained digital image signals are stored successively in the image memory 302. In accordance with correcting operations having been performed previously, the offset values and the gains of the amplifiers 301b, 301c, and 301d have been adjusted at the values for compensation for variations in output characteristics.

The correction control section 401 read the image signal having been detected by the imaging block 14a of the CCD image sensor 123 in the state, in which light is blocked from impinging upon the imaging surface 11 of the CCD image sensor 123, from the image memory 302. The correction control section 401 calculates the mean value of the signal intensities of the thus read image signal. Also, the correction control section 401 makes a judgment as to whether the calculated mean value has or has not changed by at least a predetermined value from a reference mean value. In cases where it has been judged that a change by at least the predetermined value has not occurred in the mean value of the signal intensities of the image signal described above, the correction control section 401 does not perform the re-setting of the offset values and the gain adjustment values, which act as the correction values. In such cases, the correction control section 401 erases the image signals having been detected in the state, in which light is blocked from impinging upon the imaging surface 11 of the CCD image sensor 123. Also, the ordinary image processing operation is performed on the fluorescence image, which is then detected with the imaging operation. Further, the image signal having been fed out from the image memory 302 is subjected to the digital-to-analog conversion in the digital-to-analog converter 136. The image signal obtained from the digital-to-analog converter 136 is utilized for displaying the fluorescence image 2 on the CRT display device 150.

In cases where it has been judged that a change by at least the predetermined value has occurred in the mean value of the signal intensities of the image signal described above, the correction control section 401 selects the offset values and the gain adjustment values, which correspond to the mean value, from among the offset values and the gain adjustment values having been stored in the correction value storing section 402. Also, the correction control section 401 adjusts the offset values and the gains of the amplifiers 301b, 301c, and 301d by utilizing the offset values and the gain adjustment values, which have thus been selected and which correspond to the imaging blocks 14b, 14c, and 14d. Thereafter, the correction control section 401 erases the image signals having been detected in the state, in which light is blocked from impinging upon the imaging surface 11 of the CCD image sensor 123. Also, the ordinary image processing operation is performed on the fluorescence image, which is then detected with the imaging operation. Further, the mean value having been calculated this time is set as the mean value, which acts as a new reference mean value.

With the imaging operation performed after the correction values have thus been set again, the image signals having been corrected with the new correction values are stored in the image memory 302 and utilized for displaying a fluorescence image on the CRT display device 150.

As described above, with the fourth embodiment, the offset values and the gain adjustment values acting as the correction values, which have been calculated in accordance with the variations in output characteristics among the four output channels extending from the four imaging blocks to the image memory 302 and which have been stored in the correction value storing section 402, are set in the amplifiers 301b, 301c, and 301d. Therefore, the number of pixels allocated to one output port is capable of being reduced to a value smaller than in cases where the CCD image sensor is provided with only a single output port. Therefore, even if the reading frequency is set at a Low value, signal charges of all pixels are capable of being read within the reading time. Accordingly, reading noise is capable of being suppressed and the signal-to-noise ratio of the detected image is capable of being enhanced, such that adverse effects do not occur on displaying of the fluorescence image as a dynamic image. Also, the variations in output characteristics are capable of being compensated for, and the problems are capable of being prevented from occurring in that division line patterns appear in the formed image, such that adverse effects do not occur on displaying of the fluorescence image as a dynamic image.

Also, with the fourth embodiment, amplifiers, which have heretofore been provided in a signal processing circuit, can be utilized as the correction means. Therefore, new circuit parts need not be provided, and the production cost is capable of being kept low.

Further, with the fourth embodiment, the correction value storing section 402 stores previously the mean values of signal intensities of image signals having been detected by the imaging block 14a in the state, in which light is blocked from impinging upon the imaging surface 11 of the CCD image sensor 123, and the offset values and the gain adjustment values, which act as the correction values corresponding to the respective mean values. Therefore, the processing for calculating the correction values is capable of being omitted, and the processing time required to make the compensation for the output characteristics is capable of being kept short.

In the fourth embodiment, the imaging surface 11 of the CCD image sensor 123 has the non-exposure regions. In cases where a CCD image sensor, in which the entire surface of the imaging surface 11 is utilized as the image exposure region, is employed, compensation for the output characteristics is capable of being made. However, in such cases, when the correction values are calculated, it is necessary that the offset values be calculated from the image signals having been detected in the state, in which light is blocked from impinging upon the imaging surface of the CCD image sensor, and the gain adjustment values be calculated from the image signals having been detected in the state, in which light impinges upon the imaging surface of the CCD image sensor.

In the fourth embodiment described above, the mean values of signal intensities of image signals having been detected by the imaging block 14a in the state, in which light is blocked from impinging upon the imaging surface 11 of the CCD image sensor 123, and the corresponding offset values and the corresponding gain adjustment values are stored in the correction value storing section 402. Alternatively, for example, signal intensities of image signals having been detected at a predetermined pixel in the state, in which light is blocked from impinging upon the imaging surface 11, or mean values of signal intensities of image signals having been detected by the imaging surface 11 in the aforesaid state, and the corresponding offset values and the corresponding gain adjustment values may be stored in the correction value storing section 402 In such cases, in the correction control section 401, a change in signal intensity of the image signal having been detected at the predetermined pixel or a change in mean value of signal intensities of the image signals having been detected by the imaging surface 11 may be monitored. In accordance with the results of the monitoring, a judgment may be made as to whether the re-setting of the offset values and the gain adjustment values is or is not to be performed.

Also, in the fourth embodiment, the amplifiers are employed as the correction means. Alternatively, as in the first or second embodiment of the fluorescence imaging apparatus in accordance with the present invention, a look-up table or a plurality of look-up tables may be employed as the correction means. In such cases, as in the first or second embodiment of the fluorescence imaging apparatus in accordance with the present invention, the offset values and the tone curve correction values may be employed as the correction values.

The fourth embodiment may be modified in the manner described below. Specifically, instead of the correction values being stored previously in the correction value storing section 402, when the correction values are calculated at the time of the imaging operation, the mean value of signal intensities of the image signal having been detected by the imaging block 14a in the state, in which light is blocked from impinging upon the imaging surface 11 of the CCD image sensor 123, and the corresponding correction values may be stored in the correction value storing section 402. In cases where it has been judged by the correction control section 401 that the re-calculations of the correction values are to be performed, if the correction values corresponding to the mean value of signal intensities of the image signal having been detected by the imaging block 14a at that time have been stored in the correction value storing section 402, the corresponding correction values may be utilized. If the correction values corresponding to the mean value of signal intensities of the image signal having been detected by the imaging block 14a at that time have not been stored in the correction value storing section 402, new correction values may be calculated. With the modification of the fourth embodiment, under the ordinary imaging conditions, unnecessary correction values need not be stored. Therefore, the storage capacity of the correction value storing section 402 may be set at a low value.

Figure 14:
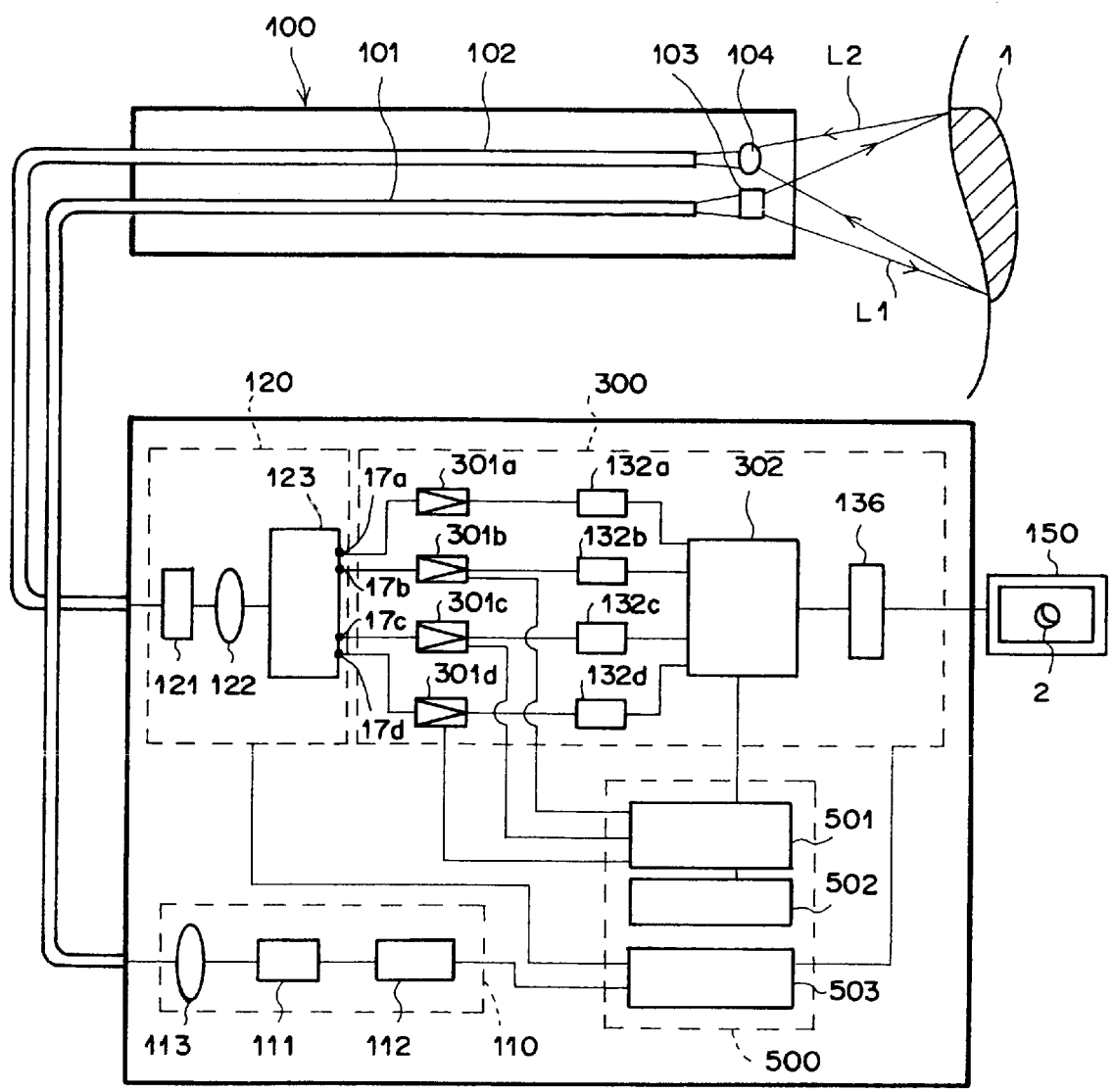
FIG. 14 is a schematic view showing an endoscope system, in which a fifth embodiment of the fluorescence imaging apparatus in accordance with the present invention is employed.

An endoscope system, in which a fifth embodiment of the fluorescence imaging apparatus in accordance with the present invention is employed, will be described hereinbelow with reference to FIG. 14. FIG. 14 is a schematic view showing the endoscope system, in which the fifth embodiment of the fluorescence imaging apparatus in accordance with the present invention is employed. In the endoscope system, excitation light is irradiated to the measuring site in a living body, and the fluorescence having been produced from the measuring site is guided through the image fiber and detected by the CCD image sensor having four output ports. In this manner, the fluorescence image is displayed on the CRT display device. When signal charges are read from the CCD image sensor, the signal charges are read at a reading frequency of 3.67 MHz, which is ¼ times as high as the conventional reading frequency. Further, each of the output ports of the CCD image sensor is provided with one of amplifiers, in which the offset values and gains are capable of being adjusted. The amplifiers perform amplification of the image signals and the compensation for the output characteristics. Also, the endoscope system is provided with a correction value storing section for storing mean values of signal intensities of image signals, which have been detected in one of the non-exposure regions, and the corresponding offset values and the corresponding gain adjustment values, which are to be set as the correction values in the amplifiers. In FIG. 14, similar elements are numbered with the same reference numerals with respect to FIG. 12.

The endoscope system, in which the fifth embodiment of the fluorescence imaging apparatus in accordance with the present invention is employed, comprises the endoscope 100 to be inserted into a region of a patient, which region is considered its being a diseased part, and the illuminating unit 110 provided with the light source for producing the excitation light, which is used for obtaining a fluorescence image. The endoscope system also comprises the imaging unit 120 for receiving the fluorescence, which has been produced from the measuring site in the living body when the excitation light is irradiated to the measuring site, and forming image signals representing the image of the fluorescence. The endoscope system further comprises the image processing unit 300 for performing image processing for displaying the fluorescence image, which has been detected by the imaging unit 120, as a visible image. The endoscope system still further comprises a control unit 500 for controlling the imaging operations. The endoscope system also comprises the CRT display device 150 for displaying the fluorescence image, which has been processed by the image processing unit 300, as a visible image.

The control unit 500 comprises a correction control section 501 for controlling the correcting operations for compensation for variations in image signal output characteristics. The control unit 500 also comprises a correction value storing section 502 for storing previously the mean values of signal intensities of image signals, which have been detected in the non-exposure region of the imaging block 14a of the imaging surface 11 of the CCD image sensor 123, and the corresponding offset values and the corresponding gain adjustment values, which act as the correction values. The control unit 500 further comprises a timing control section 503, which is connected to the respective units and controls the operation timings. The correction control section 501 is connected to the image memory 302 and the amplifiers 301b, 301c, and 301d.

The correction control section 501 read the image signal, which has been detected in the non-exposure region of the imaging block 14a of the imaging surface 11 of the CCD image sensor 123, from the image memory 302. The correction control section 501 calculates the mean value of the signal intensities of the thus read image signal. Also, the correction control section 501 makes a judgment as to whether the calculated mean value has or has not changed by at least a predetermined value from a reference mean value. In cases where it has been judged that a change by at least the predetermined value has not occurred in the mean value of the signal intensities of the image signal described above, the correction control section 501 does not perform the re-setting of the offset values and the gain adjustment values, which act as the correction values. In such cases, the ordinary image processing operation is performed.

In cases where it has been judged that a change by at least the predetermined value has occurred in the mean value of the signal intensities of the image signal described above, the correction control section 501 selects the offset values and the gain adjustment values, which correspond to the mean value, from among the offset values and the gain adjustment values having been stored in the correction value storing section 502. The offset values and the gain adjustment values having thus been selected are set as the correction values.

The amplifiers 301a, 301b, 301c, and 301d constitute the amplification means of the fluorescence imaging apparatus in accordance with the present invention. The image memory 302 constitutes the composing means of the fluorescence imaging apparatus in accordance with the present invention. The correction control section 501 constitutes the re-setting judgment means and the correction value setting means of the fluorescence imaging apparatus in accordance with the present invention. The correction value storing section 502 constitutes the correction value storing means of the fluorescence imaging apparatus in accordance with the present invention.

How the endoscope system, in which the fifth embodiment of the fluorescence imaging apparatus in accordance with the present invention is employed, operates will be described hereinbelow.

The correction value storing section 502 stores previously the mean values of signal intensities of image signals, which have been detected in the non-exposure region of the imaging block 14a, and the offset values and the gain adjustment values, which act as the correction values corresponding to the respective mean values. The image signals, from which the mean values are calculated, are the ones having been obtained with respect to various different temperatures falling within the temperature range, at which the endoscope system is used. Also, the offset values and the gain adjustment values have been calculated in the same manner as that in the calculation of the offset values and the gain adjustment values in the third embodiment of FIG. 12.

When an imaging operation is to be performed, the excitation light L1 having a wavelength of 410 nm is produced by the GaN type of semiconductor laser 111 and irradiated to the measuring site 1.

The fluorescence L2, which has been produced from the measuring site 1, passes through the image fiber 102 and impinges upon the excitation light cut-off filter 121 of the imaging unit 120. The image of the fluorescence L2 is formed on the CCD image sensor 123.

In accordance with a control signal fed from the timing control section 503, the image signals, which have been detected respectively by the imaging blocks 14a, 14b, 14c, and 14d, are read with a reading frequency of 3.67 MHz from the output ports 17a, 17b, 17c, and 17d of the CCD image sensor 123 and fed into the amplifiers 301a, 301b, 301c, and 301d of the image processing unit 300.

In the amplifiers 301a, 301b, 301c, and 301d, the image signals are amplified. The image signals, which have been amplified by the amplifiers 301a, 301b, 301c, and 301d, are digitized respectively by the analog-to-digital converting circuits 132a, 132b, 132c, and 132d. The thus obtained digital image signals are stored in the image memory 302. In accordance with correcting operations having been performed previously, the offset values and the gains of the amplifiers 301b, 301c, and 301d have been adjusted at the values for compensation for variations in output characteristics.

As in the correction control section 311 of FIG. 12, the correction control section 501 read the image signal, which has been detected in the non-exposure region of the imaging block 14a of the CCD image sensor 123, from the image memory 302. The correction control section 501 calculates the mean value of the signal intensities of the thus read image signal. Also, the correction control section 501 makes a judgment as to whether the calculated mean value has or has not changed by at least a predetermined value from a reference mean value. In cases where it has been judged that a change by at least the predetermined value has not occurred in the mean value of the signal intensities of the image signal described above, the correction control section 501 does not perform the re-setting of the offset values and the gain adjustment values, which act as the correction values. In such cases, the ordinary image processing operation is performed. Further, the image signal having been fed out from the image memory 302 is subjected to the digital-to-analog conversion in the digital-to-analog converter 136. The image signal obtained from the digital-to-analog converter 136 is utilized for displaying the fluorescence image 2 on the CRT display device 150.

In cases where it has been judged that a change by at least the predetermined value has occurred in the mean value of the signal intensities of the image signal described above, the correction control section 501 selects the offset values and the gain adjustment values, which correspond to the mean value, from among the offset values and the gain adjustment values having been stored in the correction value storing section 502. Also, the correction control section 501 adjusts the offset values and the gains of the amplifiers 301b, 301c, and 301d by utilizing the offset values and the gain adjustment values, which have thus been selected and which correspond to the imaging blocks 14b, 14c, and 14d. Further, the mean value having been calculated this time is set as the mean value, which acts as a new reference mean value.

With the imaging operation performed after the correction values have thus been set again, the image signals having been corrected with the new correction values are stored in the images memory 302 and utilized for displaying a fluorescence image on the CRT display device 150.

As described above, with the fifth embodiment, the control unit 500 is provided with the correction value storing section 502 for storing previously the mean values of signal intensities of image signals, which have been detected in the non-exposure region, and the corresponding offset values and the corresponding gain adjustment values, which act as the correction values. In cases where a change has occurred in the mean value of the image signal detected in the non-exposure region, the offset values and the gain adjustment values may be read from the correction value storing section 502 and may be set again. Therefore, the same effects as those with the fourth embodiment are capable of being obtained. Also, the change of the mean value of signal intensities of the image signal, which has been detected in the non-exposure region, can be detected by utilizing the ordinary imaging operation. Therefore, the processing for the compensation for the output characteristics is capable of being simplified.

In the fifth embodiment described above, the mean values of signal intensities of image signals, which have been detected in the non-exposure region, and the corresponding offset values and the corresponding gain adjustment values are stored in the correction value storing section 502. Alternatively, for example, signal intensities of image signals, which have been detected at a predetermined pixel in the non-exposure region, or mean values of signal intensities of image signals:, which have been detected in a predetermined area in the non-exposure region, and the corresponding offset values and the corresponding gain adjustment values may be stored in the correction value storing section 502. In such cases, in the correction control section 501, a change in signal intensity of the image signal, which has been detected at the predetermined pixel in the non-exposure region, or a change in mean value of signal intensities of the image signal, which has been detected in the predetermined area in the non-exposure region, may be monitored. In accordance with the results of the monitoring, a judgment may be made as to whether the re-setting of the offset values and the gain adjustment values is or is not -to be performed.

Also, in the fifth embodiment, the amplifiers are employed as the correction means. Alternatively, as in the first or second embodiment of the fluorescence imaging apparatus in accordance with the present invention, a look-up table or a plurality of look-up tables may be employed as the correction means. In such cases, as in the first or second embodiment of the fluorescence imaging apparatus in accordance with the present invention, the offset values and the tone curve correction values may be employed as the correction values.

The fifth embodiment may be modified in the manner described below. Specifically, instead of the correction values being stored previously in the correction value storing section 502, when the correction values are calculated at the time of the imaging operation, the mean value of signal intensities of the image signal, which has been detected in the non-exposure region of the imaging block 14a of the imaging surface 11, and the corresponding correction values may be stored in the correction value storing section 502. In cases where it has been judged by the correction control section 501 that the re-calculations of the correction values are to be performed, if the correction values corresponding to the mean value of signal intensities of the image signal, which has been detected in the non-exposure region of the imaging block 14a at that time, have been stored in the correction value storing section 502, the corresponding correction values may be utilized. If the correction values corresponding to the mean value of signal intensities of the image signal, which has been detected in the non-exposure region of the imaging block 14a at that time, have not been stored in the correction value storing section 502, new correction values may be calculated. With the modification of the fifth embodiment, under the ordinary imaging conditions, unnecessary correction values need not be stored. Therefore, the storage capacity of the correction value storing section 502 may be set at a low value.

Figure 15:
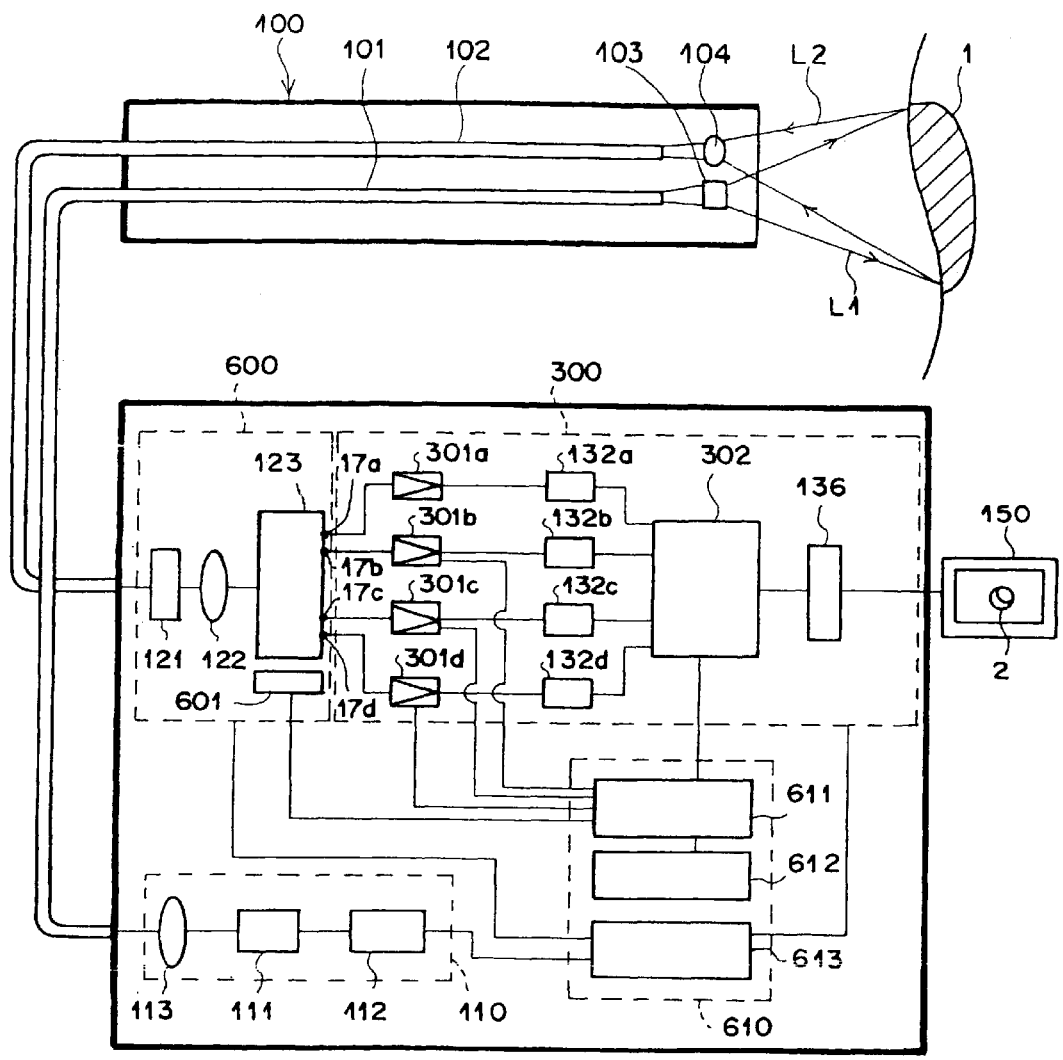
FIG. 15 is a schematic view showing an endoscope system, in which a sixth embodiment of the fluorescence imaging apparatus in accordance with the present invention is employed.

An endoscope system, in which a sixth embodiment of the fluorescence imaging apparatus in accordance with the present invention is employed, will be described hereinbelow with reference to FIG. 15. FIG. 15 is a schematic view showing the endoscope system, in which the sixth embodiment of the fluorescence imaging apparatus in accordance with the present invention is employed. In the endoscope system, excitation light is irradiated to the measuring site in a living body, and the fluorescence having been produced from the measuring site is guided through the image fiber and detected by the CCD image sensor having four output ports. In this manner, the fluorescence image is displayed on the CRT display device. When signal charges are read from the CCD image sensor, the signal charge are read at a reading frequency of 3.67 MHz, which is ¼ times as high as the conventional reading frequency. Further, each of the output ports of the CCD image sensor is provided with one of amplifiers, in which the offset values and gains are capable of being adjusted. The amplifiers perform amplification of the image signals and the compensation for the output characteristics. Also, the endoscope system is provided with a correction value storing section for storing information representing temperatures in the vicinity of the CCD image sensor, and the corresponding offset values and the corresponding gain adjustment values, which are to be set as the correction values in the amplifiers. In FIG. 14, similar elements are numbered with the same reference numerals with respect to FIG. 12.

The endoscope system, in which the sixth embodiment of the fluorescence imaging apparatus in accordance with the present invention is employed, comprises the endoscope 100 to be inserted into a region of a patient, which region is considered as being a diseased part, and the illuminating unit 110 provided with the light source for producing the excitation light, which is used for obtaining a fluorescence image. The endoscope system also comprises an imaging unit 600 for receiving the fluorescence, which has been produced from the measuring site in the living body when the excitation light is irradiated to the measuring site, and forming image signals representing the image of the fluorescence. The endoscope system further comprises the image processing unit 300 for performing image processing for displaying the fluorescence image, which has been detected by the imaging unit 600, as a visible image. The endoscope system still further comprises a control unit 610 for controlling the imaging operations. The endoscope system also comprises the CRT display device 150 for displaying the fluorescence image, which has been processed by the image processing unit 300, as a visible image.

The imaging unit 600 comprises the excitation light cut-off filter 121 for filtering out light, which has wavelengths falling within a wavelength region of at most 430 nm in the vicinity of the wavelength of the excitation light L1, from the fluorescence L2 having passed through the image fiber 102. The imaging unit 600 also comprises the CCD image sensor 123, and a thermistor 601 for detecting the temperature of the CCD image sensor 123.

The control unit 610 comprises a correction control section 611 for controlling the correcting operations for compensation for variations in image signal output characteristics. The control unit 610 also comprises a correction value storing section 612 for storing previously the information representing the temperatures of the CCD image sensor 123, and the corresponding offset values and the corresponding gain adjustment values, which act as the correction values. The control unit 610 further comprises a timing control section 613, which is connected to the respective units and controls the operation timings. The correction control section 611 is connected to the image memory 302 and the amplifiers 301b, 301c, and 301d.

This correction control section 611 receives information representing the temperature in the vicinity of the CCD image sensor 123 from the thermistor 601. Also, the correction control section 611 makes a judgment as to whether the temperature has or has not changed by at least a predetermined value from a reference temperature. In cases where it has been judged that a change by at least the predetermined value has not occurred in the temperature in the vicinity of the CCD image sensor 123, the correction control section 611 does not perform the re-setting of the offset values and the gain adjustment values, which act as the correction values. In such cases, the ordinary image processing operation is performed.

In cases where it has been judged that a change by at least the predetermined value has occurred in the temperature in the vicinity of the CCD image sensor 123, the correction control section 611 selects the offset values and the gain adjustment values, which correspond to the detected temperature, from among the offset values and the gain adjustment values having been stored in the correction value storing section 612. The offset values and the gain adjustment values having thus been selected are set as the correction values.

The amplifiers 301a, 301b, 301c, and 301d constitute the amplification means of the fluorescence imaging apparatus in accordance with the present invention. The image memory 302 constitutes the composing means of the fluorescence imaging apparatus in accordance with the present invention. The thermistor 601 constitutes the temperature detecting means of the fluorescence imaging apparatus in accordance with the present invention. The correction control section 611 constitutes the re-setting judgment means and the correction value setting means of the fluorescence imaging apparatus in accordance with the present invention. The correction value storing section 612 constitutes the correction value storing means of the fluorescence imaging apparatus in accordance with the present invention.

How the endoscope system, in which the sixth embodiment of the fluorescence imaging apparatus in accordance with the present invention is employed, operates will be described hereinbelow.

The correction value storing section 612 stores previously the information representing the temperatures in the vicinity of the CCD image sensor 123 that fall within the temperature range, at which the endoscope system is used, and the corresponding offset values and the corresponding gain adjustment values, which act as the correction values. Also, the offset values and the gain adjustment values have been calculated in the same manner as that in the calculations of the offset values and the gain adjustment values in the third embodiment of FIG. 12.

When an imaging operation is to be performed, the excitation light L1 having a wavelength of 410 nm is produced by the GaN type of semiconductor laser 111 and irradiated to the measuring site 1.

The fluorescence L2, which has been produced from the measuring site 1, passes through the image fiber 102 and impinges upon the excitation light cut-off filter 121 of the imaging unit 600. The image of the fluorescence L2 is formed on the CCD image sensor 123.

In accordance with a control signal fed from the timing control section 613, the image signals, which have been detected respectively by the imaging blocks 14a, 14b, 14c, and 14d, are read with a reading frequency of 3.67 MHz from the output ports 17a, 17b, 17c, and 17d of the CCD image sensor 123 and fed into the amplifiers 301a, 301b, 301c, and 301d of the image processing unit 300.

In the amplifiers 301a, 301b, 301c, and 301d, the image signals are amplified. The image signals, which have been amplified by the amplifiers 301a, 301b, 301c, and 301d, are digitized respectively by the analog-to-digital converting circuits 132a, 132b, 132c, and 132d. The thus obtained digital image signals are stored in the image memory 302. In accordance with correcting operations having been performed previously, the offset values and the gains of the amplifiers 301b, 301c, and 301d have been adjusted at the values for compensation for variations in output characteristics.

The correction control section 611 receives the information representing the temperature of the CCD image sensor 123 from the thermistor 601. Also, the correction control section 611 makes a judgment as to whether the detected temperature has or has not changed by at least a predetermined value from a reference temperature. In cases where it has been judged that a change by at least the predetermined value has not occurred in the temperature, the correction control section 611 does not perform the re-setting of the offset values and the gain adjustment values, which act as the correction values. In such cases, the ordinary image processing operation is performed. Further, the image signal having been fed out from the image memory 302 is subjected to the digital-to-analog conversion in the digital-to-analog converter 136. The image signal obtained from the digital-to-analog converter 136 is utilized for displaying the fluorescence image 2 on the CRT display device 150.

In cases where it has been judged that a change by at least the predetermined value has occurred in the temperature, the correction control section 611 selects the offset values and the gain adjustment values, which correspond to the detected temperature, from among the offset values and the gain adjustment values having been stored in the correction value storing section 612. Also, the correction control section 611 adjusts the offset values and the gains of the amplifiers 301b, 301c, and 301d by utilizing the offset values and the gain adjustment values, which have thus been selected and which correspond to the imaging blocks 14b, 14c, and 14d. Further, the temperature having been detected this time is set as the temperature, which acts as a new reference temperature.

With the imaging operation performed after the correction values have thus been set again, the image signals having been corrected with the new correction values are stored in the image memory 302 and utilized for displaying a fluorescence image on the CRT display device 150.

As described above, with the sixth embodiment, the thermistor 601 for detecting the temperature in the vicinity of the CCD image sensor 123 is employed. Also, the control unit 610 is provided with the correction value storing section 612 for storing previously the information representing the temperatures in the vicinity of the CCD image sensor 123 that fall within the temperature range, at which the endoscope system is used, and the corresponding offset values and the corresponding gain adjustment values, which act as the correction values. In cases where a change has occurred in the temperature of the CCD image sensor 123, the offset values and the gain adjustment values may be read from the correction value storing section 612 and may be set again. Therefore, the same effects as those with the fourth embodiment are capable of being obtained. Also, the detection of the temperature with the thermistor 601 and the comparison of the temperature with the reference temperature can be performed with a simple processing operation. Therefore, the processing for the compensation for the output characteristics is capable of being simplified.

In the sixth embodiment, the amplifiers are employed as the correction means. Alternatively, as in the first or second embodiment of the fluorescence imaging apparatus in accordance with the present invention, a look-up table or a plurality of look-up tables may be employed as the correction means. In such cases, as in the first or second embodiment of the fluorescence imaging apparatus in accordance with the present invention, the offset values and the tone curve correction values may be employed as the correction values.

The sixth embodiment may be modified in the manner described below. Specifically, instead of the correction values being stored previously in the correction value storing section 612, when the correction values are calculated at the time of the imaging operation, the information representing the temperature in the vicinity of the CCD image sensor 123 and the corresponding correction values may be stored in the correction value storing section 612. In cases where it has been judged by the correction control section 611 that the re-calculations of the correction values are to be performed, if the correction values corresponding to the temperature in the vicinity of the CCD image sensor 123, which temperature has been detected at that time, have been stored in the correction value storing section 612, the corresponding correction values may be utilized. If the correction values corresponding to the temperature in the vicinity of the CCD image sensor 123, which temperature has been detected at that time, have rot been stored in the correction value storing section 612, new correction values may be calculated. With the modification of the sixth embodiment, during the ordinary imaging operations, correction values corresponding to a temperature range, at which the endoscope system will not be used, need not be stored. Therefore, the storage capacity of the correction value storing section 612 may be set at a low value.

In the aforesaid embodiments of the fluorescence imaging apparatus in accordance with the present invention, the imaging surface 11 of the CCD image sensor 123 is divided into four imaging blocks. However, the number of the imaging blocks, into which the imaging surface 11 is divided, is not limited to for and may be set at an arbitrary value. In cases where the number of the imaging blocks, into which the imaging surface 11 is divided, is set at large value, the number of pixels, whose image signal is read from one output port, becomes small, and therefore the reading frequency can be set at a value which is small even further. Also, reading noise can be suppressed even further. Further, it becomes possible to read the image signal at an optimum reading frequency, which is associated with the minimum reading noise. However, if the number of the imaging blocks, into which the imaging surface 11 is divided, is set at large value, the peripheral circuits will become complicated, and the time required to perform the compensation processing will become long. Therefore, it is difficult for the number of the imaging blocks, into which the imaging surface 11 is divided, be set at a value larger than 64. The number of the imaging blocks, into which the imaging surface 11 is divided, should preferably fall within the range of 2 to 64.

Also, in cases where the number of the imaging blocks, into which the imaging surface 11 is divided, falls within the range of 2 to 8, the operation for compensation processing is capable of being performed with simple constitution of the peripheral circuits. Further, the reading frequency is capable of being optimized by combining the binning reading technique for adding the signal charges at a plurality of pixels and then reading the sum of the signal charges.

Further, in the aforesaid embodiments of the fluorescence imaging apparatus in accordance with the present invention, when the correction values are calculated, the offset values are calculated in accordance with the signal intensities of the image signals, which have been detected in the non-exposure regions 13, 13. Alternatively, the offset values acting as the correction values may be calculated in accordance with the image signals having been detected in the state, in which light is blocked from impinging upon the imaging surface 11, and the tone curve correction values or the gain adjustment values may be calculated in accordance with the ordinarily detected image signals having been detected in the state, in which light impinges upon the imaging surface 11. In such cases, even if the imaging surface 11 is divided into 3×3 imaging blocks, and the imaging block located at the center area of the image exposure region does not contain the non-exposure region, the offset values are capable of being calculated appropriately.

Figure 16:
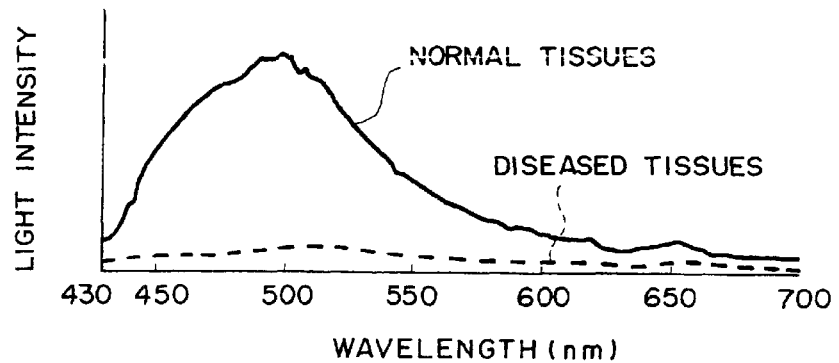
FIG. 16 is a graph showing spectral intensity distributions of fluorescence produced from normal tissues and fluorescence produced from diseased tissues.

It has heretofore been known that, in cases where the excitation light having a wavelength falling within an excitation wavelength range for an intrinsic dye in the living body is irradiated to the living body, the fluorescence spectrum varies for the fluorescence produced from the normal tissues and the fluorescence produced from the diseased tissues. FIG. 16 shows typical fluorescence spectra of the fluorescence produced from normal tissues and the fluorescence produced from diseased tissues, which fluorescence spectra have been measured by the inventors. It is assumed that the thus produced fluorescence results from superposition of the fluorescence produced by various kinds of intrinsic dyes in the living body, such as flavin, collagen, fibronectin, and porphyrin.

As described above, the spectrum of the fluorescence varies for the normal tissues and the diseased tissues. Systems for displaying location and an infiltration range of diseased tissues as a fluorescence image by the utilization of such characteristics, have heretofore been proposed. With the proposed systems, the fluorescence, which is produced from a measuring site in a living body when the excitation light is irradiated to the measuring site, is detected, and a fluorescence image, which reflects the intensity of the fluorescence or a distribution of light intensities of the fluorescence spectrum, is displayed on a monitor. Ordinarily, the proposed systems are provided with fluorescence imaging apparatuses for imaging the fluorescence, which is produced from the measuring site in the living body when the excitation light is irradiated to the measuring site. The embodiments described above are applicable to such fluorescence imaging apparatuses.

In addition, all of the contents of Japanese Patent Application Nos. 11(1999)-328413 and 2000-069101 are incorporated into this specification by reference.

What is claimed is:

1. A method of acquiring a fluorescence image, comprising the steps of:
   i) detecting intrinsic fluorescence, which has been produced from living body tissues when excitation light is irradiated to the living body tissues, with an image sensor, the excitation light causing the living body tissues to produce the intrinsic fluorescence, and
   ii) reading out the detected intrinsic fluorescence as an image,
      wherein the image is acquired by setting the image sensor such that a reading frequency, an area of one pixel, a total number of pixels, a number of pixels subjected to pixel binning, a number of reading ports, an exposure time, a quantum efficiency, an electron multiplication factor, and a sensor temperature of the image sensor satisfy the following condition formula:

$RN+DN<0.22 \times P \times H \times G$ in which RN represents the number of electric charges occurring due to reading noise, DN represents the number of electric charges occurring due to dark noise, P represents the irradiation output of the excitation light (in mW), H represents the quantum efficiency of the image sensor, and G represents the electron multiplication factor of the image sensor.

2. A method of acquiring a fluorescence image, comprising the steps of:
   i) detecting intrinsic fluorescence, which has been produced from living body tissues when excitation light is irradiated to the living body tissues, with an image sensor, the excitation light causing the living body tissues to produce the intrinsic fluorescence, and
   ii) reading out the detected intrinsic fluorescence as an image,
      wherein the image is acquired by setting the image sensor such that a reading frequency, an area of one pixel, a total number of pixels, a number of pixels subjected to pixel binning, a number of reading ports, an exposure time, a quantum efficiency, an electron multiplication factor, a sensor temperature, a floating diffusion capacity, and a full well capacity of the image sensor satisfy the following condition formulas:

$(RN+DN) \times 1000 \times G < Fd$ $(RN+DN) \times 1000 \times G < Fw$ in which RN represents the number of electric charges occurring due to reading noise, DN represents the number of electric charges occurring due to dark noise, G represents the electron multiplication factor of the image sensor, Fd represents the number of electric charges corresponding to the floating diffusion capacity, and Fw represents the number of electric charges corresponding to the full well capacity.

3. An apparatus for acquiring a fluorescence image, comprising:
   i) an image sensor for detecting intrinsic fluorescence, which has been produced from living body tissues when excitation light is irradiated to the living body tissues, the excitation light causing the living body tissues to produce the intrinsic fluorescence, and
   ii) read-out means for reading out the detected intrinsic fluorescence as an image,
      wherein the image sensor is set such that a reading frequency, an area of one pixel, a total number of pixels, a number of pixels subjected to pixel binning, a number of reading ports, an exposure time, a quantum efficiency, an electron multiplication factor, and a sensor temperature of the image sensor satisfy the following condition formula:

$$RN+DN<0.22\times P\times H\times G$$

in which RN represents the number of electric charges occurring due to reading noise, DN represents the number of electric charges occurring due to dark noise, P represents the irradiation output of the excitation light (in mW), H represents the quantum efficiency of the image sensor, and G represents the electron Multiplication factor of the image sensor.

4. An apparatus for acquiring a fluorescence image, comprising:
   i) an image sensor for detecting intrinsic fluorescence, which has been produced from living body tissues when excitation light is irradiated to the living body tissues, the excitation light causing the living body tissues to produce the intrinsic fluorescence, and
   ii) read-out means for reading out the detected intrinsic fluorescence as an image,
      wherein the image sensor is set such that a reading frequency, an area of one pixel, a total number of pixels, a number of pixels subjected to pixel binning, a number of reading ports, an exposure time, a quantum efficiency, an electron multiplication factor, a sensor temperature, a floating diffusion capacity, and a full well capacity of the image sensor satisfy the following condition formulas:

$$(RN+DN)\times 1000\times G<Fd$$

$$(RN+DN)\times 1000\times G<Fw$$

in which RN represents the number of electric charges occurring due to reading noise, DN represents the number of electric charges occurring due to dark noise, G represents the electron multiplication factor of the image sensor, Fd represents the number of electric charges corresponding to the floating diffusion capacity, and Fw represents the number of electric charges corresponding to the full well capacity.

5. An apparatus for acquiring a fluorescence image as defined in claim 3 or 4 wherein the reading frequency is set so as to satisfy the condition RN=DN.

6. An apparatus for acquiring a fluorescence image as defined in claim 3 or 4 wherein the image sensor is a charge coupled device type of image sensor.

7. An apparatus for acquiring a fluorescence image as defined in claim 3 or 4 wherein the image sensor is a metal oxide semiconductor type of image sensor.

8. A fluorescence imaging apparatus, comprising:
   i) irradiation means for irradiating excitation light to a measuring site, the excitation light causing the measuring site to produce fluorescence, and
   ii) imaging means for detecting the fluorescence, which has been produced from the measuring site, the imaging means being provided with an imaging surface, which comprises a plurality of pixels arrayed in a two-dimensional form,
      wherein the imaging means is provided with a plurality of output ports,
      wherein the imaging surface is divided into N number of imaging blocks, where N is at least 2,
      each of the output ports is provided for one of the N number of imaging blocks, and
      the fluorescence imaging apparatus further comprises:
         composing means for combining image signals, which have been outputted from the output ports, to form an image signal representing one image,
         correction value calculating means for calculating correction values in accordance with variations in output characteristics among N number of output channels, which extend on the N number of imaging blocks to the composing means,
         correction means for performing compensation for the variations in output characteristics, and
         correction value setting means for setting the correction values in the correction means.

9. A fluorescence imaging apparatus as defined in claim 8 wherein the correction means is constituted of signal transforming means, which stores offset values and tone curve correction values.

10. A fluorescence imaging apparatus as defined in claim 9 wherein the imaging surface of the imaging means is constituted of an image exposure region and non-exposure regions,
   each of the imaging blocks contains one of the non-exposure regions,
   the correction value calculating means calculates the offset values, which act as the correction values, from image signals having been detected in a state, in which light impinges upon the imaging surface of the imaging means, and having been outputted through the respective output channels, the offset values being calculated such that signal intensities of image signals, which have been detected respectively in the non-exposure regions of the imaging blocks, take approximately identical values, and
   the correction value calculating means calculates the tone curve correction values, which act as the correction values, from the image signals having been detected in the state, in which light impinges upon the imaging surface of the imaging means, and having been outputted through the respective output channels, the tone curve correction values being calculated such that signal intensities of image signals, which have been detected respectively at adjacent ends of the imaging blocks that are adjacent to each other, take approximately identical values.

11. A fluorescence imaging apparatus as defined in claim 9 wherein the correction value calculating means calculates the offset values, which act as the correction values, from image signals having been detected in a state, in which light is blocked from impinging upon the imaging surface of the imaging means, and having been outputted through the respective output channels, the offset values being calculated such that signal intensities of image signals, which have been detected respectively in the imaging blocks, take approximately identical values, and
   the correction value calculating means calculates the tone curve correction values, which act as the correction values, from image signals having been detected in a state, in which light impinges upon the imaging surface of the imaging means, and having been outputted through the respective output channels, the tone curve correction values being calculated such that signal intensities of image signals, which have been detected respectively at adjacent ends of the imaging blocks that are adjacent to each other, take approximately identical values.

12. A fluorescence imaging apparatus as defined in claim 8 wherein the correction means is constituted of amplification means, in which offset values and gains are capable of being adjusted.

13. A fluorescence imaging apparatus as defined in claim 12 wherein the imaging surface of the imaging means is constituted of an image exposure region and non-exposure regions, each of the imaging blocks contains one of the non-exposure regions, the correction value calculating means calculates the offset values, which act as the correction values, from image signals having been detected in a state, in which light impinges upon the imaging surface of the imaging means, and having been outputted through the respective output channels, the offset values being calculated such that signal intensities of image signals, which have been detected respectively in the non-exposure regions of the imaging blocks, take approximately identical values, and the correction value calculating means calculates gain adjustment values, which act as the correction values, from the image signals having been detected in the state, in which light impinges upon the imaging surface of the imaging means, and having been outputted through the respective output channels, the gain adjustment values being calculated such that signal intensities of image signals, which have been detected respectively at adjacent ends of the imaging blocks that are adjacent to each other, take approximately identical values.

14. A fluorescence imaging apparatus as defined in claim 12 wherein the correction value calculating means calculates the offset values, which act as the correction values, from image signals having been detected in a state, in which light is blocked from impinging upon the imaging surface of the imaging means, and having been outputted through the respective output channels, the offset values being calculated such that signal intensities of image signals, which have been detected respectively in the imaging blocks, take approximately identical values, and the correction value calculating means calculates the gain adjustment values, which act as the correction values, from image signals having been detected in a state, in which light impinges upon the imaging surface of the imaging means, and having been outputted through the respective output channels, the gain adjustment values being calculated such that signal intensities of image signals, which have been detected respectively at adjacent ends of the imaging blocks that are adjacent to each other, take approximately identical values.

15. A fluorescence imaging apparatus as defined in claim 9, 10, 11, 12, 13, or 14 wherein the imaging surface of the imaging means is constituted of an image exposure region and non-exposure regions, the fluorescence imaging apparatus further comprises re-setting judgment means for making a judgment for each imaging operation and as to whether re-setting of the correction values is to be or is not to be performed, the judgment being made in accordance with the presence or absence of a change in signal intensity of an image signal, which has been detected in one of the non-exposure regions, the correction value calculating means operates such that, in cases where it has been judged by the re-setting judgment means that the re-setting of the correction values is to be performed, the correction value calculating means calculates new correction values, and the correction value setting means sets the new correction values, which have been calculated by the correction value calculating means, as the correction values in the correction means.

16. A fluorescence imaging apparatus, comprising:

i) irradiation means for irradiating excitation light to a measuring site, the excitation light causing the measuring site to produce fluorescence, and ii) imaging means for detecting the fluorescence, which has been produced from the measuring site, the imaging means being provided with an imaging surface, which comprises a plurality of pixels arrayed in a two-dimensional form, wherein the imaging means is provided with a plurality of output ports, wherein the imaging surface is divided into N number of imaging blocks, where N is at least 2, each of the output ports is provided for one of the N number of imaging blocks, and the fluorescence imaging apparatus further comprises:

composing means for combining image signals, which have been outputted from the output ports, to form an image signal representing one image, correction value storing means for storing correction values for compensation for variations in output characteristics, the correction values having been calculated in accordance with the variations in output characteristics among N number of output channels, which extend from the N number of imaging blocks to the composing means, correction means for performing compensation for the variations in output characteristics, and correction value setting means for setting the correction values in the correction means.

17. A fluorescence imaging apparatus as defined in claim 16 wherein the correction means is constituted of signal transforming means, which stores offset values and tone curve correction values, and the correction value storing means stores the offset values and the tone curve correction values as the correction values.

18. A fluorescence imaging apparatus as defined in claim 16 wherein the correction means is constituted of amplification means, in which offset values and gains are capable of being adjusted, and the correction value storing means stores the offset values and gain adjustment values as the correction values.

19. A fluorescence imaging apparatus as defined in claim 16, 17, or 18 wherein the correction value storing means stores signal intensity or a mean value of signal intensities of an image signal having been detected in a state, in which light is blocked from impinging upon the imaging surface of the imaging means, and corresponding correction values, the fluorescence imaging apparatus further comprises re-setting judgment means for making a judgment for each imaging operation and as to whether re-setting of the correction values is to be or is not to be performed, the judgment being made in accordance with the presence or absence of a change in signal intensity or a mean value of signal intensities of an image signal having been detected in a state, in which light is blocked from impinging upon the imaging surface of the imaging means, and the correction value setting means operates such that, in cases where it has been judged by the re-setting judgment means that the re-setting of the correction values is to be performed, the correction value setting means reads the correction values, which correspond to the signal intensity or the mean value of signal intensities of the image signal associated with the judgment in that the re-setting of the correction values is to be performed, from among the correction values having been stored in the correction value storing means and sets the correction values, which have thus been read from the correction value storing means, as the correction values in the correction means.

20. A fluorescence imaging apparatus as defined in claim 16, 17, or 18 wherein the imaging surface of the imaging means is constituted of an image exposure region and non-exposure regions, the correction value storing means stores signal intensity or a mean value of signal intensities of an image signal, which has been detected in one of the non-exposure regions, and corresponding correction values, the fluorescence imaging apparatus further comprises re-setting judgment means for making a judgment for each imaging operation and as to whether re-setting of the correction values is to be or is not to be performed, the judgment being made in accordance with the presence or absence of a change in signal intensity or a mean value of signal intensities of an image signal, which has been detected in one of the non-exposure regions, and the correction value setting means operates such that, in cases where it has been judged by the re-setting judgment means that the re-setting of the correction values is to be performed, the correction value setting means reads the correction values, which correspond to the signal intensity or the mean value of signal intensities of the image signal associated with the judgment in that the re-setting of the correction values is to be performed, from among the correction values having been stored in the correction value storing means and sets the correction values, which have thus been read from the correction value storing means, as the correction values in the correction means.

21. A fluorescence imaging apparatus as defined in claim 16, 17, or 18 wherein the correction value storing means stores information representing a temperature in the vicinity of the imaging means and corresponding correction values, which have been calculated by the correction value calculating means, the fluorescence imaging apparatus further comprises:
temperature detecting means for detecting the temperature in the vicinity of the imaging means, and
re-setting judgment means for making a judgment for each imaging operation and as to whether re-setting of the correction values is to be or is not to be performed, the judgment being made in accordance with the presence or absence of a change in temperature in the vicinity of the imaging means, and
the correction value setting means operates such that, in cases where it has been judged by the re-setting judgment means that the re-setting of the correction values is to be performed, the correction value setting means reads the correction values, which correspond to the temperature in the vicinity of the imaging means associated with the judgment in that the re-setting of the correction values is to be performed, from among the correction values having been stored in the correction value storing means and sets the correction values, which have thus been read from the correction value storing means, as the correction values in the correction means.

22. A fluorescence imaging apparatus as defined in claim 8, 9, 10, 11, 12, 13, 14, 16, 17, or 18 wherein the value of N is at most 64.

23. A fluorescence imaging apparatus as defined in claim 8, 9, 10, 11, 12, 13, 14, 16, 17, or 18 wherein the value of N is at most 8.

* * * * *